United States Patent
Kriger

(10) Patent No.: US 10,525,849 B2
(45) Date of Patent: Jan. 7, 2020

(54) TECHNOLOGY AND METHODS OF ON-BOARD VEHICLE OCCUPANT ACCURATE WEIGHING BY A SIMPLIFIED WEIGHING APPARATUS BASED ON WEIGHING MODERATOR AND ITS APPLICATIONS IN ON-BOARD OCCUPANT WEIGHING SYSTEMS

(71) Applicant: Yefim G. Kriger, Ansonia, CT (US)

(72) Inventor: Yefim G. Kriger, Ansonia, CT (US)

( * ) Notice: Subject to any disclaimer, the term of this patent is extended or adjusted under 35 U.S.C. 154(b) by 0 days.

(21) Appl. No.: 16/366,440

(22) Filed: Mar. 27, 2019

(65) Prior Publication Data
US 2019/0217741 A1 Jul. 18, 2019

Related U.S. Application Data

(62) Division of application No. 15/430,219, filed on Feb. 10, 2017, now Pat. No. 10,245,973, which is a (Continued)

(51) Int. Cl.
*G01G 19/414* (2006.01)
*G16H 50/30* (2018.01)
(Continued)

(52) U.S. Cl.
CPC .......... *B60N 2/002* (2013.01); *A61B 5/6893* (2013.01); *B60R 21/01512* (2014.10);
(Continued)

(58) Field of Classification Search
CPC .... G01G 19/08; G01G 19/12; G01G 19/4142; A61B 5/6893; B60N 2/002; B60R 21/01512
See application file for complete search history.

(56) References Cited

U.S. PATENT DOCUMENTS 5,515,933 A 5/1996 Meyer et al.
5,763,837 A 6/1998 Davignon et al.
(Continued)

OTHER PUBLICATIONS

Automobiles Brakes Tutorial downloaded from Carparts website Apr. 12, 2016.
(Continued)

*Primary Examiner* — Natalie Huls

(57) ABSTRACT

An on-board vehicle occupant weighing technology includes a simplified vehicle occupant weighing apparatus based on the discovered horwest effect and weighing moderator. The simplified weighing apparatus utilizes a weighing unit connected to the car seat of the vehicle occupant and a further weighing moderator, which provides convenient weighing of the foot part of the occupant's body by the same weighing unit that is connected to the car seat. The technology employs several methods of the weight measurements provided by different moderator approaches. The technology, methods, and simplified weighing apparatus are employed in on-board vehicle overweight and obesity preventing system wherein a weight trend analyzer provides predicting possibility of the occupant's overweight or obesity in a short predetermined period of time and automatically warning a vehicle occupant and a health care provider of the condition. The technology may also provide an accurate and convenient occupant's weight measurement in the vehicle safety devices such as seat belt and air bag Supplemental Restraint System (SRS system) to improve the Occupant Classification System to prevent possible extra force applied to the occupant's body in case of collision.

5 Claims, 9 Drawing Sheets

Related U.S. Application Data division of application No. 14/282,715, filed on May 20, 2014, now Pat. No. 9,566,877.

(60) Provisional application No. 61/956,059, filed on May 30, 2013.

(51) Int. Cl.
| | |
|---|---|
| *G01G 19/12* | (2006.01) |
| *G01G 19/44* | (2006.01) |
| *B60N 2/00* | (2006.01) |
| *A61B 5/00* | (2006.01) |
| *B60R 21/015* | (2006.01) |
| *G06F 19/00* | (2018.01) |
| *G16H 30/20* | (2018.01) |
| *G16H 40/63* | (2018.01) |

(52) U.S. Cl.
CPC ......... *G01G 19/12* (2013.01); *G01G 19/4142* (2013.01); *G01G 19/44* (2013.01); *G06F 19/321* (2013.01); *G06F 19/3418* (2013.01); *G16H 30/20* (2018.01); *G16H 40/63* (2018.01); *G16H 50/30* (2018.01)

(56) References Cited

U.S. PATENT DOCUMENTS

| | | | |
|---|---|---|---|
| 5,986,221 A | 11/1999 | Stanley | |
| 6,076,853 A | 6/2000 | Stanley | |
| 6,181,996 B1 | 1/2001 | Chou et al. | |
| 6,242,701 B1 | 6/2001 | Breed et al. | |
| 6,345,839 B1 | 2/2002 | Kuboki et al. | |
| 6,448,890 B1 | 9/2002 | Cooper | |
| 6,585,328 B1 | 7/2003 | Oexman et al. | |
| 6,649,848 B2 | 11/2003 | Kriger | |
| 6,816,807 B2 | 11/2004 | Kriger | |
| 7,134,715 B1 | 11/2006 | Fristedt et al. | |
| 7,330,784 B2 | 2/2008 | Johnson et al. | |
| 7,465,272 B2 | 12/2008 | Kriger | |
| 7,774,212 B2 | 8/2010 | Huang et al. | |
| 7,803,111 B2 | 9/2010 | Kriger | |
| 7,910,840 B2 | 3/2011 | Chai | |
| 8,388,532 B2 | 3/2013 | Morgan | |
| 8,417,422 B2 | 4/2013 | Choi et al. | |
| 8,552,661 B2 | 10/2013 | Kriger | |
| 9,566,877 B2 | 2/2017 | Kriger | |
| 10,131,308 B2 * | 11/2018 | Kriger | B60R 21/01546 |
| 2001/0033074 A1 | 10/2001 | Aoki et al. | |
| 2002/0003344 A1 | 1/2002 | Maeda | |
| 2003/0042051 A1 | 3/2003 | Kriger | |
| 2003/0130595 A1 | 7/2003 | Mault | |
| 2004/0148127 A1 | 7/2004 | Kriger | |
| 2005/0101875 A1 | 5/2005 | Semler et al. | |
| 2005/0194192 A1 | 9/2005 | Kriger | |
| 2007/0185391 A1 | 8/2007 | Morgan | |
| 2007/0244375 A1 | 10/2007 | Jenkins et al. | |
| 2008/0046152 A1 | 2/2008 | Ohtake et al. | |
| 2008/0046291 A1 | 2/2008 | Huang et al. | |
| 2008/0093143 A1 | 4/2008 | Harrison | |
| 2008/0294370 A1 | 11/2008 | Kriger | |
| 2009/0132099 A1 | 5/2009 | Kriger | |
| 2009/0182204 A1 | 7/2009 | Semler et al. | |
| 2009/0314556 A1 | 12/2009 | Harris | |
| 2010/0138078 A1 | 6/2010 | Choi et al. | |
| 2010/0327638 A1 | 12/2010 | Petereit et al. | |
| 2011/0096558 A1 | 4/2011 | Kriger | |
| 2011/0183870 A1 | 7/2011 | Pan et al. | |
| 2012/0312604 A1 | 12/2012 | Fujii | |
| 2013/0011819 A1 | 1/2013 | Horseman | |
| 2013/0012786 A1 | 1/2013 | Horseman | |
| 2013/0012790 A1 | 1/2013 | Horseman | |
| 2013/0013327 A1 | 1/2013 | Horseman | |
| 2013/0117040 A1 | 5/2013 | James et al. | |
| 2013/0218487 A1 | 8/2013 | Fujii et al. | |
| 2014/0163333 A1 | 6/2014 | Horseman | |
| 2014/0239980 A1 | 8/2014 | Ootaka | |
| 2014/0275834 A1 | 9/2014 | Bennett | |
| 2014/0353048 A1 | 12/2014 | Kriger | |
| 2016/0096498 A1 | 4/2016 | Kubota | |
| 2016/0163319 A1 | 6/2016 | Parundekar et al. | |
| 2017/0151892 A1 | 6/2017 | Kriger | |

OTHER PUBLICATIONS

Guo et al. "Predicting overweight and obesity in adulthood from body mass index values in childhood and adolescence 1-3" 2002.
Magarey et al. "Predicting obesity in early adulthood from childgood and parental obesity" 2003.
Nyhol et al. "The Validity of Obesity Based on Self-reported Weight and Height: Implications for Population Studies" 2007.

* cited by examiner

| Adult weight gain from normal to overweight and obese status | | | | | | |
|---|---|---|---|---|---|---|
| Weight status | Normal | Overweight | | Normal | Obese | |
| BMI | 22 | 27 | 22 →27 | 22 | 32 | 22 →32 |
| | Weight, Lb | | Weight gain | Weight, Lb | | Weight gain |
| Height | | | | | | |
| 4'10'' (58'') | 105 | 129 | 24 | 105 | 153 | 48 |
| 4'11'' (59'') | 109 | 133 | 24 | 109 | 158 | 49 |
| 5'0'' (60'') | 112 | 138 | 26 | 112 | 163 | 51 |
| 5'1'' (61'') | 116 | 143 | 27 | 116 | 169 | 53 |
| 5'2'' (62'') | 120 | 147 | 27 | 120 | 175 | 55 |
| 5'3'' (63'') | 124 | 152 | 28 | 124 | 180 | 56 |
| 5'4'' (64'') | 128 | 157 | 29 | 128 | 186 | 58 |
| 5'5'' (65'') | 132 | 162 | 30 | 132 | 192 | 60 |
| 5'6'' (66'') | 136 | 167 | 31 | 136 | 198 | 62 |
| 5'7'' (67'') | 140 | 172 | 32 | 140 | 204 | 64 |
| 5'8'' (68'') | 144 | 177 | 33 | 144 | 210 | 66 |
| 5'9'' (69'') | 149 | 182 | 33 | 149 | 216 | 67 |
| 5'10'' (70'') | 153 | 188 | 35 | 153 | 222 | 69 |
| 5'11'' (71'') | 157 | 193 | 36 | 157 | 229 | 72 |
| 6'0'' (72'') | 162 | 199 | 37 | 162 | 235 | 73 |
| 6'1'' (73'') | 166 | 204 | 38 | 166 | 242 | 76 |
| 6'2'' (74'') | 171 | 210 | 39 | 171 | 249 | 78 |
| 6'3'' (75'') | 176 | 216 | 40 | 176 | 256 | 80 |

Source of data in black : Evidence Report of Clinical Guidelines on the Identification, Evaluation, and Treatment of Overweight and Obesity in Adults, 1998.NIH/National Heart, Lung. and Blood Institute (NHLBI). Centers for Disease Control and Prevention United States Department of Health and Human Services

FIG. 7

TECHNOLOGY AND METHODS OF ON-BOARD VEHICLE OCCUPANT ACCURATE WEIGHING BY A SIMPLIFIED WEIGHING APPARATUS BASED ON WEIGHING MODERATOR AND ITS APPLICATIONS IN ON-BOARD OCCUPANT WEIGHING SYSTEMS

CROSS REFERENCE TO RELATED APPLICATIONS

This application is a divisional of U.S. patent application Ser. No. 15/430,219 filed on Feb. 10, 2017, which is a divisional application of U.S. patent application Ser. No. 14/282,715 filed on May 20, 2014 now U.S. Pat. No. 9,566,877 which issued on Feb. 14, 2017 which claims the benefit of U.S. Provisional Application No. 61/956,059 filed May 30, 2013, the contents each of which are incorporated herein by reference thereto.

FIELD OF THE INVENTION

Various embodiments of the present invention are directed to technology, methods, and a simplified weighing apparatus in order to provide a simplified, accurate, and convenient weighing of the vehicle occupant's body by using a weighing moderator.

BACKGROUND OF THE INVENTION

The problem of overweight and obesity has now become a nation-wide problem for the USA and other countries. More than 60% of Americans are overweight (see websites of American Obesity Association, Centers for Disease Control, etc.) and most are car occupants. There are a number of weight control systems and methods to lose weight. Many weight control plans are available to individual users, from which the user can select a particular program designed to control the weight of that individual. Associated with such programs are nutrition programs and programs involving exercise and like physical activities.

Many different kinds of electrical scales have also been suggested for diet and weight control plans. These plans require the dieter to have a scale on the floor at home or another weighing facility and have a regular weighing procedure. Thus the dieter has to find time to step up on the scale. As a result, the diet and weight control plans do not help a dieter who is busy and highly active to choose a diet and lose weight and keep healthy. These activities often depend on a mood, physical state, and free time of the individual. As a result, an individual very often does not obey the requirements of the lose weight program and exercise plans on time or does not accomplish them.

There is a possibility to employ an on-board vehicle weight control system that weighs and memorizes weight of a vehicle occupant when one sits down on a driver or a passenger seat. By collecting an on-board vehicle occupant's weight each driver and/or passenger in a car could get help to prevent possible overweight and obesity because a lot of measurements made in a vehicle relatively to the few measurements during follow up doctor visits make possible to use statistical methods of predicting overweight and obesity. It is the principal object of this system to extend the utility of a motor vehicle, especially a passenger vehicle such as an automobile, a van, school bus, corporate vehicle or bus, limousine, tourist bus, truck, and even a boat, so that the time spent in the vehicle can be utilized more efficiently and the interaction of the vehicle with the driver and/or passenger can be improved.

There is also a problem to accurately weigh a vehicle occupant in other on-board systems. For example, accurately weighing vehicle occupants in on-board vehicle supplemental restraint system provides a possibility of an accurate control of the airbag inflation force depending on a real value of the occupant's weight and eliminates extra force applied to the occupant's body at the time of collision.

To weigh a vehicle occupant, it is necessary to weigh a body part in a car seat and a foot part of his/her weight. It takes two weighing devices, and makes weighing of the vehicle occupant complicated. A simplified method of weighing is to use only one weighing device to weigh a body part in a car seat. Contribution of the weight of the foot part of the body to a total weight of a vehicle occupant may be evaluated by several ways: to prompt a vehicle occupant to lift up and keep his/her legs out from the floor and away from the pedals during the weight measurement (this solution is not convenient because lifting up the feet may not be habitual for some people), correlate total weight of the occupant's body by position of the feet on the floor (this solution is not accurate), etc.

All described above on-board vehicle systems and methods to accurately weigh a vehicle occupant are not convenient or are complicated.

SUMMARY OF THE INVENTION

One embodiment of the present invention relates to a vehicle having a system that weighs an occupant, such as an on-board overweight and obesity preventing system that analyzes the weight progress of a person, forecasting overweight or obesity that may begin in a short period of time (in several months or later) and provides information to the person and to a health care professional to prevent possible overweight or obesity of the person. It may also be used to provide an accurate occupant's weight measurement in the vehicle safety devices such as seat belt and air bag Supplemental Restraint System (SRS system) to prevent extra force applied to the occupant's body in case of collision.

In one embodiment, a simplified weighing apparatus and methods for accurately weighing an individual in a vehicle that is employed in an on-board overweight and obesity preventing system that avoids drawbacks of earlier methods and systems and which can be practiced more conveniently than earlier methods and systems is provided.

In another embodiment, an apparatus and method for eliminating the need for separate measuring of the occupant's foot weight is provided. Still further, an apparatus and method are provided to enable application of a physical effect that was discovered by the inventor of this application, Dr. Yefim G. Kriger, PhD. The discovered effect states that the value of a weight measurement of an object located in a closed system on a weighing unit does not change while said object providing a bi-directional force in a horizontal direction of a predetermined value to a vertical surface of another object, which is a predetermined distance away. This physical effect related to the STability of the weight measurement of the object on a weighing unit, while providing a predetermined force in a HORizontal direction to another object, described in U.S. Provisional Application Ser. No. 61/956,059 filed on May 30, 2013 and was referred to as a weighor effect. In the present application, the name of this effect has been changed to HORWEST (HORizontal WEighing STability) effect. In addition, the inventor has also changed the name of the One-Scale On-board Overweight and Obesity Preventing Technology (OSOPT) to (KEF) convenient Kemoder Elimination of a separate occupant's Feet weighing technology.

In another embodiment the method wherein said horwest effect provides an accurate weight measurement of an occupant sitting on the seat, to which a weighing unit is operatively attached, by employing a horizontal piece that is hanging from a vertical part of the vehicle and secures the foot of the occupant while being compressed by it in a horizontal direction, and this compressing does not influence the accurate weight of the occupant's whole body measurement by said weighing unit at the time when a switch connected to said horizontal piece signals to the computing and control unit that the foot of the vehicle occupant compresses it and the current result of the weight measurement is correct.

In yet another embodiment, a method of weighing a person sitting in a seat of a vehicle employing an effect described herein as the horwest effect is provided. The method provides an accurate weighing of the person sitting on the seat through a weighing unit that is operatively coupled to the seat of the vehicle.

In yet another embodiment, an on-board occupant weighing system located in a vehicle is provided. The system having: a weighing unit operatively connected to a seat of a vehicle, wherein the weighing unit is configured to provide an output indicative of an occupant's weight when they are seated on the seat; a computing and control unit operatively coupled to the weighing unit; a switch operatively coupled to the computing and control unit, the switch being located behind a vertical surface of the vehicle proximate to the seat, wherein the switch is configured to provide an output when a force is applied to the surface of the vehicle proximate to the switch, wherein the computing and control unit only processes the output from the weighing unit when the output of the switch is received by the computing and control unit.

BRIEF DESCRIPTION OF THE DRAWINGS

The above and other objects, features, and advantages will become more readily apparent from the following description, reference being made to the accompanying drawing in which:

FIG. 7 is a table of adults' weight gain from a normal to overweight and obese weight statuses;

DETAILED DESCRIPTION

Figure 1:
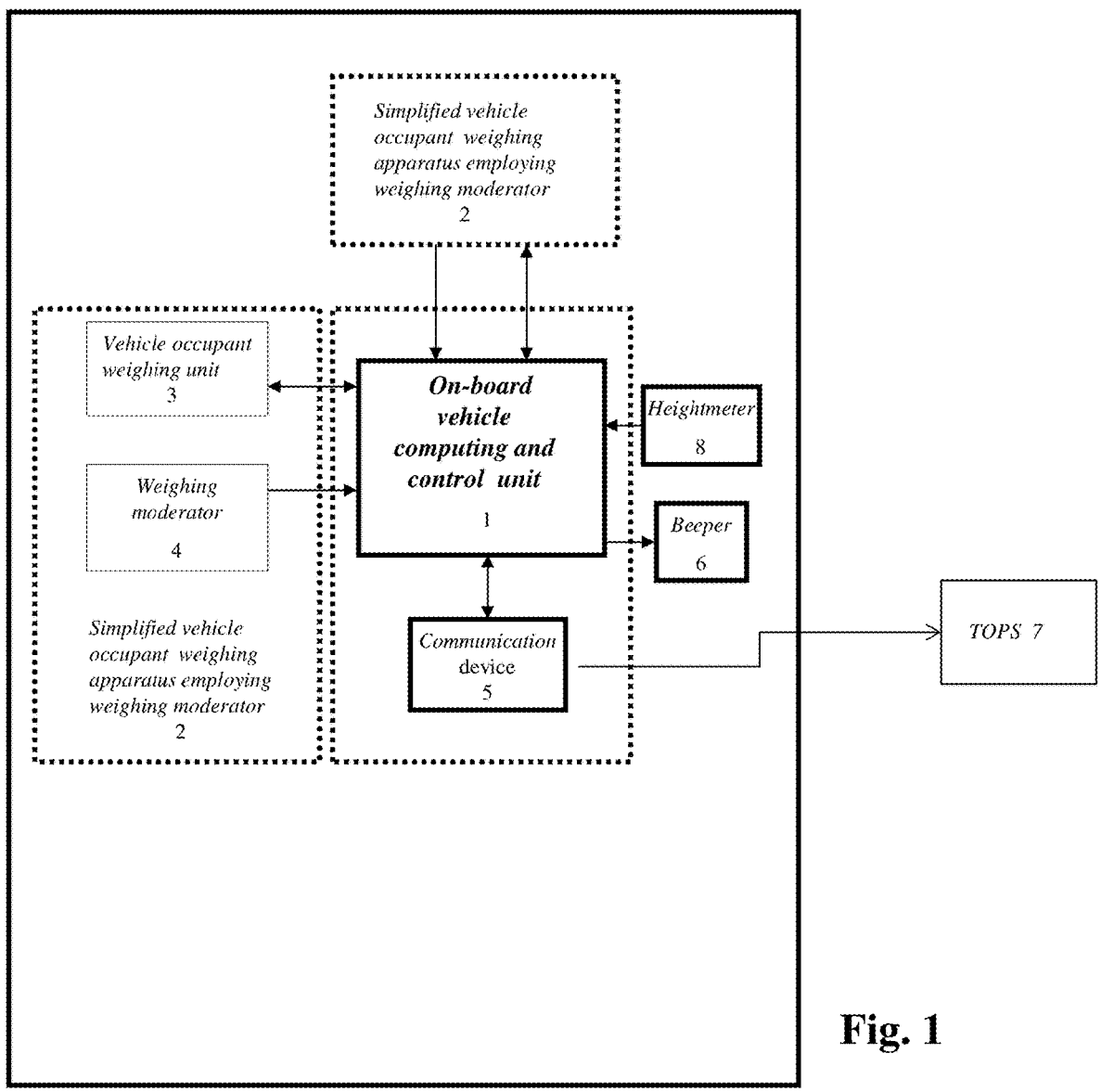
FIG. 1 is an outlined block diagram of the devices that comprise the on-board vehicle overweight and obesity preventing system.

Reference is also made to the following patents and/or patent applications: U.S. Pat. Nos. 6,649,848; 6,816,807; 7,465,272; U.S. Patent Application No. 2008/0294370; and U.S. Provisional Patent Application No. 60/939,810 the contents each of which are incorporated herein by reference thereto.

Various embodiments of the present invention will become apparent hereinafter are attained, in accordance with the invention, in an automotive vehicle equipped with technology for weighing an occupant with the overweight and obesity preventing system that includes a more convenient and simplified weighing apparatus and methods of a vehicle occupant weighing by employing only one weighing unit for the vehicle occupant's convenient weighing, and provided with the ability to analyze a weight trend, detect possible overweight or obesity of the vehicle occupant in a short predetermined period of time, and to send a warning to the vehicle occupant and to a health care professional to prevent possible overweight or obesity. The invention utilizes an on-board vehicle computing and control unit which includes microcontroller facilities and smartphone wireless capabilities in any variation or may employ facilities of an on-board computer.

Prior to the present invention, there was no technology that provides an overweight and obesity preventing system with a convenient, simplified, and accurate weighing apparatus for weighing of a vehicle occupant.

A principal object of the present invention is the on-board vehicle occupant weighing technology that provides the on-board vehicle overweight and obesity preventing system with an improved weighing apparatus and methods of weighing an individual in a vehicle based on a discovered physical effect called a horwest effect that states: the value of a weight measurement of an object located in a closed system on a weighing unit doesn't change while said object provides a bi-directional force in a horizontal direction of a predetermined value to a vertical surface of another object, which is a predetermined distance away. The horwest effect is used to implement the simplified weighing apparatus for vehicle occupant weighing. An existence of the horwest effect is easy to demonstrate by the following experiment.

Put any human body weighing scale (postal electrical scale or mechanical scale with continual weight measurements will be the best) against the wall. Step onto the scale and check your weight. Touch a wall very gently by an arm pressing the wall in a horizontal direction. If you push the wall in a horizontal direction with a force up to 10 to 30 lb, the display of the postal electrical scale or mechanical scale with the continual weight measurements will show approximately the same value of your weight that you measured before pushing the wall. If you use any digital human body floor weighing scale, make several measurements and find out your average body weight. Before making an experiment with the wall, calibrate the scale. Before stepping onto the scale, push the wall very gently by your hand in a horizontal direction, and step onto the scale. The scale display will show approximately the same value of your weight if you push the wall in a horizontal direction with a force up to 10 to 30 lb.

As the horwest effect description states, an object located on a weighing platform does not change the value of its weight measurement if the force provided by this object is applied in a horizontal direction to a vertical surface of another object. If the force is not applied horizontally, a vertical component of an applied force will influence the weight measurement of the object and will corrupt the weight measurement of the object on the weighing platform.

Let us make a couple of definitions:

1. Hocpoint (a point of a vehicle Compressed or stretched in a HOrizontal direction) is a sensitive point or area of a vertical piece of a vehicle, which according to the horwest effect does not change the occupant's weight measurement if the vehicle occupant compresses or stretches it in a horizontal direction, and this activity according to the third Newton's law produces a force that provides an occupant support to conveniently lift up and keep out from the floor his/her feet during the weight measurement. There are at least several convenient hocpoints in a vehicle.

2. The simplest on-board vehicle weighing apparatus may be designed by utilizing only one weighing unit connected to the car seat of the vehicle occupant and pushing feet to a vertical surface of above mentioned piece of the vehicle in a horizontal direction because pushing feet to a vertical surface of another object in a horizontal direction will conveniently secure them on another object and will not influence the weight measurement of the vehicle occupant according to the horwest effect. Theoretically, it is possible to design such simplified weighing apparatus to accurately weigh the vehicle occupant and just simply push his/her feet horizontally against a substance such as a passive flat vehicle vertical piece. But to employ such weighing apparatus to accurately weigh the vehicle occupant and just push his/her feet against a substance such as a passive flat vehicle vertical surface in a strongly horizontal direction is impractical because the vehicle occupant is not able to push the feet against any vehicle surface during the measurement in exactly a horizontal direction. The problem may be solved by designing and employing a part that secures the vehicle occupant's pushing feet and redirects a feet pushing force in a horizontal direction. This part is a weighing moderator and is a Key Element that Moderates two problems: a vehicle occupant's feet securing and controlling the feet force in a horizontal direction. This weighing moderator is called a kemoder.

Basic kemoder is a point or area that includes at least one hocpoint compressed or stretched by a vehicle occupant in a horizontal direction. More advanced kemoder has to provide a horizontal redirection for the force created by the vehicle occupant while compressing or stretching a spring or any elastic substance, such as a rubber, included in the kemoder.

3. Low level weighing moderator (LLK kemoder) is the kemoder that may be pressed by a low part of the vehicle occupant's body (foot or leg).

4. High level weighing moderator (HLK kemoder) is the kemoder that may be pressed (dragged) by an upper part of the vehicle occupant's body (finger, palm, nape of the head, or elbow) and is located above the occupant's waist.

The present invention provides a convenient Kemoder Elimination of a separate occupant's Feet weighing (KEF) technology that enables application of a simplified weighing apparatus based on the horwest effect and employs only one weighing unit.

In another embodiment weighing moderator comprising of a horizontal piece and secured on it at least one spring or any elastic, such as a rubber or any other substance, through which a vehicle occupant's foot or other occupant's part of body compresses said vertical part of a vehicle in a horizontal direction, and said spring or substance, secured horizontally relative to the ground and perpendicularly to said piece, redirects a compressing force of an occupant in a horizontal direction or weighing moderator is retractable from underneath a high car seat and may comprise of a horizontal spring, through which the weighing moderator pushes a back side of the occupant's leg up forward in a horizontal direction, and said weighing moderator is "hanging" from the firewall or from other vertical part of the vehicle and its position is adjustable, and there is a footrest combined with a weighing moderator and such a piece is a pedal that moderates a convenient position of the occupant's feet and accurately weighs the occupant and provides a horizontal movement of the pedal while the occupant's foot is pressing the pedal during the weight measurement, and position of this pedal is adjustable, and there is a switch inside of this weighing moderator, and this switch signals to the computing and control unit that the foot is secured on the weighing moderator while compressed.

In another embodiment the system wherein the weighing moderator comprising of a horizontal piece, on which are secured knuckle-joint and spring or any elastic, such as a rubber or any other substance, and a vehicle occupant's foot compresses a knuckle-joint, which in turn, compresses in a horizontal direction a vertical part of a vehicle, and adding a knuckle-joint to this row of compressing units redirects a compressing force of an occupant's foot applied to the vertical part of the vehicle in a horizontal direction more accurate, which provides more accurate weighing a vehicle occupant in a seat by a weighing unit attached to the seat; and there is a switch inside of this weighing moderator, and this switch signals to the computing and control unit that the foot is secured on the weighing moderator while compressed.

In another embodiment vertical surface through which a vehicle occupant's foot or other occupant's part of body compresses said vertical piece, and said spring or substance, secured horizontally relative to the ground and perpendicularly to said piece, redirects a compressing force of an occupant in a horizontal direction or weighing moderator is retractable from underneath a high car seat and may comprise of a horizontal spring, through which the weighing moderator pushes a back side of the occupant's leg up forward in a horizontal direction, and said weighing moderator is "hanging" from the firewall and its position is adjustable, and there is a footrest combined with a weighing moderator and such a piece is a pedal that moderates a convenient position of the occupant's feet and accurately weighs the occupant and provides a horizontal movement of the pedal while the occupant's foot is pressing the pedal during the weight measurement, and position of this pedal is adjustable, and there is a switch inside of this weighing moderator, and this switch signals that the foot is secured on the weighing moderator while compressed.

There are at least several following approaches to use the horwest effect and convenient kemoder elimination of a separate feet weighing KEF technology in the applications that provide the on-board obesity preventing system with a simplified and accurate weighing apparatus that employs only one weighing unit, which is connected to the seat of the vehicle occupant: low level kemoder approach, high level kemoder approach, elbow high level kemoder approach, nape high level kemoder approach, high level back kemoder approach, combined low and high level kemoder approach.

Low Level Kemoder Approach.

In accordance with an exemplary embodiment of the present invention, the proposed on-board vehicle weighing apparatus may comprise of a weighing unit connected to the car seat of the driver or passenger and a Low Level weighing moderator (LLK kemoder) upon which the feet of the vehicle occupant may be placed.

Another exemplary embodiment of the present invention is that the simple low level kemoder is a point or an area of a vertical piece of a vehicle upon which the feet of the vehicle occupant are placed horizontally during a weight measurement.

Yet another exemplary embodiment of the present invention is that the low level kemoder may comprise of a vertical piece and a horizontal spring or any elastic, such as a rubber, substance upon which the feet of the vehicle occupant are placed, and which is fixed on the vertical piece of the kemoder.

In addition, and as yet another exemplary embodiment of the present invention, is that the long axis of the kemoder's spring or any elastic substance is placed horizontal to the ground and perpendicular to the vertical piece of the kemoder.

In still yet another exemplary embodiment of this invention is that the low level kemoder can be "hanging" from the firewall (bulkhead) or "standing" on the floor.

Yet another exemplary embodiment of the present invention is that the vertical piece of the low level kemoder is secured on a footrest or on a pedal and its position is adjustable.

Yet another exemplary embodiment of the present invention is that there is a footrest combined with a low level kemoder and such a piece is a pedal that MODERates a convenient position of the occupant's FEet and accurately weighs the occupant and provides a horizontal movement of the pedal while the occupant's foot is pressing the pedal during the weight measurement, and this pedal is a FeModer (femoder) and its position is adjustable, and there is a switch inside this femoder, which signals that the foot is secured on the femoder. In still yet another exemplary embodiment of this invention is that the kemoder's spring or elastic substance is placed strongly perpendicular to its vertical piece and redirects a compressing (stretching) force of an occupant in a horizontal direction to this piece.

Yet another exemplary embodiment of the present invention is that the low level kemoder is retractable from underneath a high car seat and may comprise of a horizontal spring through which the kemoder pushes from behind a back side of the occupant's foot forward in a horizontal direction.

Yet another exemplary embodiment of the present invention is that the low level kemoder may comprise of a vertical piece, a spring, and a knuckle-joint through which the feet of the vehicle occupant compress the spring that is fixed on the vertical piece of the kemoder.

Of course, there may be other solutions for the low level kemoder that secures the vehicle occupant compressing feet and redirects a pushing force in a strongly horizontal direction.

Another feature of the present invention provides the accuracy of weighing of an occupant in a vehicle by analyzing a set of the occupant weight measurements acquired during a period of time from a moment when the occupant sits down in a car seat and compresses the LLK kemoder by foot to a moment of time when a signal of the weight measuring end appears.

The following weighing procedure is provided for weighing an occupant in a vehicle with low level kemoder approach:

When you sit down in the car seat, put your feet on the kemoder near your feet and wait for a signal about the end of the weight measurement.

High Level Kemoder Approach.

Let us now discuss an application that employs a high level weighing moderator (HLK kemoder) approach by pressing (dragging) horizontally by driver's finger a kemoder located on a vertical piece of the dashboard or steering wheel (high level kemoder) in front of the driver. As follows from the horwest effect description, the driver in a car seat will not influence his/her weight measurement by pressing (dragging) in a horizontal direction the kemoder located on a vertical part of the dashboard or steering wheel. In contrast, the driver gets the possibility to use the force created according to the third Newton's law by pressing (dragging) the high level kemoder as a support force to more easily and conveniently lift and keep feet up from the floor during the weight measurement. As result, the foot part of the occupant's weight will not need its separate measurement because it will be automatically included in the total body weight measured by the same one-platform weighing unit that is connected to the car seat according to the KEF technology described above.

In another embodiment a method of weighing an on-board vehicle occupant employing a computing and control unit that comprising a microcontroller and a communication device, and further having a weighing apparatus, which provides a vehicle occupant's weight measurement, that includes a weighing unit that is connected to the car seat of a vehicle occupant and the weighing moderators secured on a vertical parts of a steering wheel, dashboard, front doors, header of the car seat, on the driver and/or front passenger seatbacks, and each of said weighing moderator having a switch sending a signal to the computing and control unit while have been compressed, comprising the steps of: compressing a weighing moderator, which switch starts sending a signal to the computing and control unit while have been compressed, the computing and control unit by receiving a signal from the weighing moderator turns on a beeper and starts to monitor the output of the weighing unit, listening the sounds of the beeper and continuing to compress the weighing moderator, the occupant is moving feet up from any surface and is keeping them in the air until there are sounds of the beeper, analyzing the occupant's weight measurements provided by its microcontroller connected to the output of the weighing unit, computing and control unit collects needed number of occupant weight samples when the measurements are stable, processing collected data by computing and control unit and turning off the beeper if the result of the occupant's weight measurement is reasonable.

Another exemplary embodiment of the present invention, which employs a high level kemoder approach, may comprise of the kemoder located on a vertical piece of the dashboard against the front passenger of the car, and the front passenger of the vehicle presses (drags) this kemoder in a horizontal direction by a finger or palm and produces a force, which provides him/her a support to conveniently lift up his/her feet during the weight measurement.

Another exemplary embodiment of the present invention is that it employs a high level kemoder on the horizontal strip of the internal part of the left and right front doors nearby the handles against to the left elbow of the driver (left front door) and to the right elbow of the front passenger (right front door). In this Elbow High Level Kemoder (EHLK) approach, by pressing these kemoders on the doors (which surface is close to a vertical shape) by left elbow (driver) or by right elbow (front passenger), the vehicle occupant can produce a force that helps to conveniently lift and keep feet up from the floor during the weight measurement while the value of the weight measurement of the occupant will not change during weighing according to the horwest effect.

Another exemplary embodiment of the present invention is that it employs a high level kemoder approach and improves accuracy of the occupant's body weighing by a kemoder located on the back of the car seat against the occupant's back. This High level Back Kemoder (HBK) is fixed inside of the back of the car seat or secured inside of a pad that covers a back of the car seat against the occupant's back. The HBK kemoder may comprise of a number of springs (or elastic substances) secured horizontally on the back of the car seat and perpendicularly to the occupant's back and prevents, according to the horwest effect, the weight measurement from error if the back of the occupant touches the back of the car seat during the weight measurement.

In another embodiment is the system wherein the weighing moderator is a vertical part of the seatback of the car seat, to which a weighing unit is connected, closest to the occupant's back or said back weighing moderator secured inside the seatback against the occupant's back or fixed inside of a pad that covers a seatback against the occupant's back, and this weighing moderator may comprise of a number of springs (or elastic substances) secured on the seatback horizontally and perpendicularly to the occupant's back and prevents the occupant weight measurement from error if the back of the occupant touches the seatback during the weight measurement, and there is another weighing moderator, which is located on the occupant's seatback headrest, that is retractable from the headrest of the car seat, and which has a vertical front part, and touching said header weighing moderator prevents an eventual error (caused by the occupant's spine touching the seatback) by occupant's back limited movement to the seatback after sensing said header weighing moderator, and said header weighing moderator does not influence the vehicle occupant weight measurement while being pushed by the nape of the occupant's head in a horizontal direction.

Yet another exemplary embodiment of the present invention is a Nape of Head High Level (NHL) kemoder, which has a vertical front part and is located on the occupant's seatback headrest and is retractable from the headrest of the car seat, and touching said kemoder prevents an eventual error (caused by the occupant's spine touching the seatback) by occupant's back limited movement to the seatback after sensing said kemoder, and said kemoder does not influence the vehicle occupant weight measurement while being pushed by the nape of the occupant's head in a horizontal direction.

Another exemplary embodiment of the present invention is that it employs a High level Back Kemoder (HBK) approach by the manufacturer making a seatback vertical in the area where the back of the occupant touches the back of the car seat while sitting in it.

In another embodiment is a weighing moderator wherein depending on a chosen method of the vehicle occupants weighing the weighing moderators are secured on the dashboard, steering wheel, firewall, door, seatback, and header where the car manufacturer provides small vertical areas for said weighing moderators, and choosing an appropriate spring or elastic substance for them from different kind of type, size, shape, strength, material, etc. for different type of a vehicle, height of a car seat, weight and height category of the occupants in a vehicle that provides the accuracy and convenience of the occupant weighing in a vehicle.

Another exemplary embodiment of the present invention that employs a high level kemoder approach may comprise of the kemoder located on any vertical part of the vehicle in front of the occupant. The vehicle occupant presses it in a horizontal direction by a finger or palm and produces a force, which provides him/her a support to conveniently lift up his/her feet during the weight measurement.

In addition, and as yet another exemplary embodiment of the present invention that employs a high level kemoder approach, is that the long axis of the kemoder's spring or elastic substance is placed horizontally, and the vehicle occupant compresses horizontally the kemoder located on any vertical part of the vehicle at the right angle to this part.

Another exemplary embodiment of the present invention that employs a high level kemoder approach is that at least one rear row seat passenger occupies a car seat that is separated from the car rear row passenger seat bench. For example, larger passenger vehicles can include rear row (second row or third row) seating arrangements having two seats for three passengers. This rear row seating arrangement includes one single passenger seat and one multi-passenger seat, where the multi-passenger seat can be a seat known as a 60/40 seat. This second row single passenger seat may have an occupant body weighing apparatus, and this occupant has convenient access to press (drag) a high level kemoder secured on a vertical part of the back of a driver or front passenger car seat. In this case, the second row single passenger seat occupant has a possibility to use the force created by pressing (dragging) the high level kemoder as a support force to more easily and conveniently lift and keep feet up from the floor during his/her weight measurement. As result, the foot part of the second row single passenger seat occupant's weight will not need its separate measurement because it will be automatically included in the total body weight measured by the same weighing unit that is connected to the second row single passenger seat weighing unit that is connected to his/her back car seat according to the KEF technology described above.

In another embodiment is a technology wherein said weighing apparatus may comprise of a weighing unit connected to a second row single passenger seat of a large passenger vehicle (that is separated from the car back passengers seat bench), and the weighing moderator of this weighing apparatus is secured on a vertical piece of a front seatback that is against said second row single passenger seat, and the occupant of said second row single passenger seat has convenient access to compress (stretch) said weighing moderator of said weighing apparatus, which is secured on a vertical area of the driver or front passenger seatback, and the second row single passenger seat occupant employs the force created according to the third Newton's law by horizontally pressing (dragging) said weighing moderator as a support force to conveniently lift and keep feet up from the vehicle floor during said occupant weight measurement, and the foot part of the second row single passenger seat occupant's weight will not need its separate measurement because it will be automatically included in the total body weight measured by the same weighing unit that is connected to said second row single passenger seat according to said technology, and said single passenger seat may be in the third rear row also, and said weighing unit in any vehicle seat is calibrated for more accurate weight measurement at predetermined time by one or more predetermined value weights, whose values are inputted into the computing and control unit by the operator of a vehicle or by a representative of the car service in the calibration mode, and a correction for footwear is made according to the statistics about the weight of the shoes and clothing that depends on the occupant's weight, age, and also seasonal ambient temperatures, or by measurement of the occupant's footwear or clothing directly in the vehicle, and the value of correction of errors of weight measurement from the occupant's seat belt and from the slight touching of a brake pedal by a driver's right foot are found and inputted into the computing and control unit once before starting to use the vehicle for each occupant in his/her seat, and this repeated in predetermined time. The correction by these values is made during the regular weight measurements.

Yet another exemplary embodiment of the present invention is that there are more than one HLK kemoder in the system.

The following weighing procedure is provided for weighing an occupant in a vehicle with high level kemoder approach: Sit down in the car seat, push at least one the closest kemoders on the steering wheel or dashboard, and simultaneously lift your feet up and keep them from the floor during weighing.

Another feature of the present invention provides the accuracy of weighing of an occupant in a vehicle by analyzing a set of the occupant weight measurements acquired during a period of time from a moment when the occupant sits down in a car seat and compresses (drags) the HLK kemoder to a moment of time when a signal of the weight measuring end appears.

Combined Low and High Level Kemoder Approach.

In addition, and as yet another exemplary embodiment of the present invention is that it employs both LLK and HLK together. By compressing a HLK located on the dashboard, the vehicle occupant produces a force, which provides him/her a support to easily and conveniently lift up from the floor his/her feet during the weight measurement. Compressing the LLK by feet in a horizontal direction in this approach will be much easier because the vehicle occupant produced a force by HLK, which provided him/her by extra support to easily and conveniently lift his/her feet up during the weight measurement. As result, the foot part of the vehicle occupant's weight will not need its separate measurement because it will be automatically included in the total body weight measured by the same weighing unit that is connected to the car seat.

Another feature of the present invention provides the accuracy and convenience of weighing of an occupant in a vehicle by choosing an appropriate spring or elastic substance for the kemoder from different kinds of type, size, shape, strength, material, etc. for different types of vehicle, height of a car seat, weight and height category of the occupants in a vehicle.

Another feature of the present invention is that the car manufacturer provides the vertical areas on dashboard and steering wheel for the high level kemoders and convenient access to them by a driver or passenger in a vehicle that provides the accuracy and convenience of weighing of an occupant in a vehicle. Another feature of the present invention provides the accuracy of weighing of an occupant in a vehicle by securing the spring or elastic piece of the kemoder partially down inside of a cylinder, which is fixed on the kemoder to get a strong horizontal direction of the force while compressing the kemoder.

Another feature of the present invention is that there is a switch inside of the cylinder, in which the spring or elastic piece of the kemoder is secured, that starts a process of weight measurement while an occupant presses the kemoder at the time of the weight measurement.

Another feature of the present invention is that there is a switch inside of the kemoder that starts a process of weight measurement while compressing the kemoder by an occupant at the time of the weight measurement.

In another embodiment is a weighing moderator wherein said spring or elastic piece of the weighing moderator secured partially down inside of a cylinder, which is fixed on the vertical piece of the weighing moderator to get a strong horizontal redirection of the force produced while compressing the weighing moderator, and there is a switch inside of said weighing moderator, and this switch starts a process of weight measurement by sending a signal to a computing and control unit while compressing the weighing moderator by an occupant at the time of the weight measurement, and a passenger in a car seat, to which a weighing unit is connected, is allowed to weigh himself/herself independently from a driver by pushing weighing moderator when a vehicle is stopped at a STOP sign or at the red light at the intersection, and said switch in the weighing moderator triggers the weight measurement, and a number of daily measurements for each passenger is restricted by a predetermined value.

Yet another exemplary embodiment of the present invention is that a passenger in a car seat, to which a weighing unit is connected, is allowed to weigh him/herself independently from a driver by pushing a low level kemoder (employing the low level kemoder approach) or by pushing a high level kemoder (employing a high level kemoder approach) when a vehicle is stopped (a speed of the vehicle is zero) at a STOP sign or at the red light at the intersection, and a switch in the kemoder starts the weight measurement, and a number of daily measurements for each passenger is restricted by a predetermined value.

Yet another exemplary embodiment of the present invention is that it provides accurate and convenient on-board weighing for all possible categories of human beings by age groups:

1. (Category B)—Babies and small children—children up to 6-8 years age, who are carried in a car in their own booster seats and whose weight is not greater than 40-80 lb (The weight and height described in this and next paragraphs are different in the regulations of the different USA states).

These children may be weighed and their height measured before putting them in a child booster seat by putting and weighing them in any seat (see FIG. 5), to which the weighing unit of appropriate capacity to weigh children is connected ("Child place"), and heightmeter is attached to a ceiling above the "Child place". The height of a baby or small child is calculated as a difference of distances from the heightmeter to a seat and from the heightmeter to a baby or small child's head that stays vertically on the: Child place" car seat. There is a restriction to measure the height of tall children by the distance from the ceiling to the car seat.

After his/her weight and height (rarely) are measured, the baby or small child is conveniently put back in his/her child booster seat until it beeps to show that the belt(s)/clip(s) are securely buckled. A weighing unit in the "Child place" may be eventually substituted by a weighing unit of a different capacity depending on the vehicle operator child's weight;

2. (Category C)—Children and adolescents whose weight greater than 40-80 lb and who use a regular car seat but whose feet do not touch the car floor while sitting in the car seat. These children may be weighed on any car seat that has a weighing apparatus while a car is in parked position;

3. (Category A) Adults and teenagers whose feet touch a car floor while sitting in the car seat. These occupants may be weighed in a parked vehicle on a driver or front passenger car seat or any other seat that has a weighing unit attached to the car seat by employing any of kemoder approach and KEF technology.

In another embodiment is a method of operating an on-board vehicle overweight and obesity preventing system providing an engineering approach and employing a simplified weighing apparatus, which provides a vehicle occupant's weight measurement, having a weighing unit that is connected to the car seat of a vehicle occupant, and the weight of foot part of the occupant's body is conveniently provided by the same weighing unit that is connected to the car seat, and said system further having the computing and control unit including a microcontroller and a smartphone or/and sharing resources of the on-board computer or any other unit with computing and control resources adequate to needed resources, and said method comprising the steps of: registering and receiving said vehicle occupant's personal information in the computing and control unit, wherein said microcontroller and smartphone share said personal information; choosing from the menu "Choose an occupant to weigh" the name of the occupant and the position or the number of the car seat in which said occupant is sitting or automatically monitoring by said microcontroller or smartphone all seats to which the weighing units are connected; conveniently eliminating the need to separately weigh the feet of a tall child, adolescent, or adult occupant whose feet touch the floor while said occupant is sitting in said car seat; measuring said occupant's weight by a simplified weighing apparatus having a weighing unit connected to the car seat of said occupant; receiving the occupant's weight with said microcontroller and/or a smartphone; showing a graph of weight or BMI trend of an occupant on the screen of the computing and control unit at the discretion of the operator of the vehicle; sending the result of the weight measurement of registered occupant to a Trend Obesity Preventing Service; determining the probability of overweight or obesity in a predetermined short period of time of registered occupant by weight trend analyzer executed by said microcontroller or smartphone; upon forecasting overweight or obesity, to send a warning about said overweight or obesity to said occupant or parent locally and to occupant's primary doctor by a wireless communication device.

In addition, and as yet another exemplary embodiment of the present invention is that it employs a school bus as a part of the school obesity preventing system. This bus may comprise of at least one student car seat with attached weighing unit according to the convenient elimination of a separate feet weighing KEF technology. There is also a heightmeter on the ceiling of the bus controlled by the microcontroller, and a driver of the bus takes care of the student weight and height (in a certain period of time) measuring procedures. The result of the measurement is wirelessly sent to the school Trend Obesity Preventing Service (TOPS) and to the student's parent and driver's smartphones. The data of the current measurements on the driver's smartphone will be erased after the next consecutive measurement.

In another embodiment a method of operating an on-board vehicle overweight and obesity preventing system wherein a vehicle is a school bus that is a part of the school obesity preventing system or said bus is a healthcare facility bus, employing at least two simplified weighing apparatuses in each said bus for students weight measurement wherein each apparatus having a weighing unit that is connected to a student bus seat and these weighing units have different capacity, which covers a reasonable span of the students' weights in said buses, and the weight of said student's feet is conveniently provided by the same weighing unit that is connected to said student bus seat according to convenient elimination of a separate feet weighing based on weighing moderator technology, and there is also a heightmeter for measuring the height of a student in the seat, and a certified school bus driver with a smartphone or healthcare professional in a healthcare facility bus equipped with a computing and control unit takes care of the student weight and height (in a certain period of time) measuring procedures and said method comprising the steps of: receiving said bus student's personal information, wherein said computing and control unit stores said personal information; measuring weight of said bus student by a simplified weighing apparatus, having a weighing unit that is connected to the seat of said bus student and conveniently eliminating the separate weighing of said bus student's feet by employing said based on weighing moderator technology; measuring height of said bus student by a heightmeter in said bus; receiving the bus student's weight and height with said computing and control unit; sending the result of the weight and height measurements of said bus student to the school Trend Obesity Preventing Service or to the same service of the Global Obesity Preventing System; determining the probability of overweight or obesity in a predetermined short period of time of said student by weight trend analyzer that analyzes a lot of weight measurement statistic data; upon forecasting overweight or obesity sending a warning about said overweight or obesity to the student's parent, to the school nurse, and to the student's primary health care provider; erasing the previous weight measurements of said school bus student from the driver's smartphone.

In another embodiment a method of operating an on-board vehicle overweight and obesity preventing system wherein an occupant of said system is a baby or small child, and said system further having a heightmeter located on the ceiling of the vehicle above the "Child place" car seat and connected to said microcontroller, and said method comprising the steps of: receiving said vehicle occupant's personal information, wherein said microcontroller and smartphone share said personal information; conveniently putting a baby or small child on a vehicle seat to which a weighing unit of appropriate capacity is connected, and this weighing unit will be eventually substituted by a weighing unit of a different capacity depending on the vehicle operator child's weight; choosing from the menu "Choose an occupant to weigh" the name of said baby or small child and the position or number of the car seat in which said baby or small child is put; measuring said baby or small child occupant's weight; receiving the occupant's weight with said microcontroller or a smartphone; measuring by a heightmeter a distance to a seat to which a weighing unit of appropriate capacity is connected; making a baby or small child stay on the seat of the "Child place"; measuring by a heightmeter a distance to the occupant's head; receiving the occupant's height with said microcontroller or a smartphone; putting a baby or small child back to his/her booster seat and getting the beep that the belts of the booster seat are buckled promptly; sending the results of the weight and height (rarely) measurements of said occupant to a Trend Obesity Preventing Service; determining the probability of overweight or obesity in a predetermined short period of time of said occupant by weight trend analyzer executed by said microcontroller or smartphone; upon forecasting overweight or obesity, sending a warning about said overweight or obesity to a parent of said baby or small child locally and to said baby or small child's primary doctor by a wireless communication device.

The inventor designed a simple and chip prototype of an ultrasound heightmeter for measuring the height of a baby and small child vehicle occupant and a school bus student, which he uses at home.

In another embodiment is a method of operating an on-board vehicle overweight and obesity preventing system wherein a vehicle is a corporate vehicle or bus, limousine, even tourist bus as a part of the obesity preventing system, employing a simplified weighing apparatus for occupant weight measurement having a weighing unit that is connected to at least one car seat in said vehicle and the weight of foot part of an occupant of said car seat is conveniently provided by the same weighing unit that connected to said car seat according to elimination of a separate feet weighing based on weighing moderator technology, and each registered occupant of said vehicle further takes care of his/her weight measuring procedure by his/her smartphone and said method comprising the steps of: receiving said car seat occupant personal information, wherein said smartphone stores said personal information; measuring weight of said occupant by a simplified weighing apparatus having a weighing unit that is connected to said car seat and conveniently eliminating the separate weighing of said occupant's feet by employing based on weighing moderator technology; receiving the occupant's weight with said computing and control unit; showing a graph of weight or BMI occupant's trend on the screen of his/her smartphone at his/her discretion; sending the result of the weight measurement of registered occupant to the Trend Obesity Preventing Service; determining the probability of overweight or obesity in a predetermined short period of time of said car seat registered occupant by weight trend analyzer executed by said smartphone; upon forecasting overweight or obesity sending a warning about said overweight or obesity to said occupant locally on the screen of the smartphone and to occupant's primary doctor at user's discretion wirelessly by said smartphone.

In another embodiment is a technology of an on-board vehicle occupant weighing, based on weighing moderator that includes of a simplified weighing apparatus having only one weighing unit connected to the seat of the vehicle occupant and further having a weighing moderator and comprising the following steps of an on-board vehicle occupant weighing: choosing an occupant to weigh by the "Choose an occupant to weigh" routine located in the computing and control unit; monitoring existence of an occupant in a car seat by the weighing unit; monitoring state of the weighing moderators fixed in the vehicle by a routine downloaded to the computing and control unit; measuring occupant's weight by a simplified weighing apparatus having only one weighing unit connected to the seat of the vehicle occupant and controlled by a microcontroller of the computing and control unit; conveniently eliminating the need to separately weigh the feet of occupant in the previous step by pressing in horizontal direction weighing moderators that according to the horwest effect and the Newton's third law create a force that is used by the occupant as a support force to conveniently keep feet's weight from the vehicle floor during said occupant weight measurement, and the foot part of the occupant's weight will be automatically included in the total body weight measured by the same weighing unit that is connected to the occupant's seat.

Yet another exemplary embodiment of the present invention is that it provides the driver a very prospective and transparent method of automatically weighing him/her in a vehicle that is leaving a garage, driveway, or parking lot or is coasting along. The method of MEasuring the weight of a Driver Automatically in a vehicle Leaving a garage, driveway, or parking lot (MEDAL method) or is coasting along is very effective because the driver doesn't receive any instructions or prompts during weighing, and his/her activities and movements are regular and standard. In this case, the driver will be weighed automatically by using the following signals:

1. A signal $S_1$ from a switch that is inside of the kemoder, while the left foot is pushing an adjustable vertical surface of such a hanging LLK kemoder or said left foot is pushing such a LLK kemoder secured on the footrest or on a hanging pedal.

2. A signal $S_2$ from a regular brake switch, which turns on a brake light and other devices of a vehicle when a driver pushes a brake pedal. According to the horwest effect, using a hanging vertical pedal or secured on the footrest LLK kemoder and HLK kemoders secured on the steering wheel doesn't influence the driver's weight measurement by pushing the adjustable vertical surfaces of the kemoders horizontally while automatically and accurately weighing the driver by the MEDAL method at the time when the vehicle is leaving a garage, driveway, or parking lot or is coasting along.

In another embodiment the technology wherein it provides a method of measuring weight of a driver automatically in a running vehicle that is leaving a garage, driveway, or parking lot and is moving at the idle speed or in a vehicle coasting along at the time when the driver controls the vehicle by releasing and pressing a vertical surface of the brake pedal by the right foot while the left foot is pushing an adjustable vertical surface of a hanging pedal with weighing moderator, or said left foot is pushing weighing moderator secured on a pedal, floor, or footrest, and the driver's hands are on the weighing moderators secured on the steering wheel, and there are a switch downward next to the brake pedal and a switch downward next to the gas pedal to eliminate an erroneous weight measurement.

It may be also a switch downward next to the brake pedal and switch downward next to the gas pedal to eliminate a possible erroneous weight measurement when the driver shifts the right foot from the brake pedal or from the gas pedal downward to the next floor during leaving a garage, driveway, or parking lot or coasting along.

In another embodiment is a simplified on-board vehicle weighing apparatus comprising: a vehicle occupant weighing unit, an on-board vehicle computing and control unit, and a weighing moderator; said weighing unit is connected to a vehicle occupant seat and provides weighing of a whole driver's body in a running vehicle; said computing and control unit includes a microcontroller and a wireless communications device, which may be a smartphone, receiving a signal of weight measurements from said microcontroller through a wireless network and transmitting processed data through a wireless network to an on-board system that employs said simplified on-board vehicle weighing apparatus; said microcontroller continuously monitors a weighing unit and memorizes samples of the weight measurement; said wireless communications device has all needed routines installed and continuously monitors position and state of the gear selector, brake, gas, and weighing moderator pedals, switches, weighing unit, etc.; the weighing moderator, on which left foot of the driver is located, has a switch that signals if the left foot pushes said moderator and this weighing moderator is secured on a hanging vertical pedal or on the footrest and according to a horwest effect does not change the weight measurement of the driver while being pushed horizontally by the left foot, and this foot will be on said weighing moderator out of floor and this effect provides accurate and convenient weighing of the whole driver's body including the weight of the foot part of driver's body by the same weighing unit connected to a vehicle occupant seat in a running vehicle; said computing and control unit signals to weighing unit to start weighing a driver in a vehicle leaving a garage, driveway, or parking lot when the gear selector is in Drive or Reverse position and the brake pedal is released by the right foot of the driver and the vehicle starts to move at the idle speed from the garage, driveway, or parking lot, and the right foot of the driver slightly touches the brake pedal or it is in the air, and computing and control unit continues to check if the gas pedal is not pressed and a speed of the vehicle is less than a predetermined value, and the switches downward next to the brake or gas pedals are not pressed to eliminate erroneous weight measurements; the weighing unit continues to weigh the driver, and if the brake pedal is released during a time that is longer than time of one weight measurement, the control and computing unit will get one sample of driver's weight, the output number of the samples counter will be increased by one, timer will be reset, and weighing unit will start a next measurement of the driver's weight, and every time the driver releases the brake pedal, the weighing apparatus starts to weigh a driver until the brake pedal will be pressed again, and because the left foot is on a footrest or a pedal, on which weighing moderator is secured, and hands of the driver are on the steering wheel, on which high level weighing moderators are secured, the weight measurement of the driver according to the horwest effect will not be practically disturbed, and reasonable accurate driver weight measurement will be done; and if during the next weight measurement the brake pedal will be pressed by the right foot of the driver before than the time of one weight measurement elapsed, the control and computing unit removes the current sample of the weight measurement, and if the number of samples is not enough, the weight measurement procedure will be continued when the brake pedal will be released again and said driver will be weighed several times by on-board simplified weighing apparatus during time intervals when said driver releases the brake pedal (or sequentially releases and pushes the brake pedal several times by right foot) to get the needed number of the samples counted by the sample counter, and the number of collected weight samples will be processed by the computing and control unit, and during processing of collected data the maximum value of the successful measured weight will be employed in the result; the described algorithm of weighing a driver in a running vehicle may work not only during leaving a garage, driveway, or parking lot, but when a vehicle is coasting along on the road too.

Everybody can check how it is convenient to lift feet from the car floor by simultaneously compressing a vertical or virtually vertical area on the dashboard or steering wheel of a vehicle by a finger. This effect makes weighing a vehicle occupant a very accurate, simple, fast, and convenient procedure in a car seat with a weighing unit connected to the seat by use of the KEF technology. That means that the KEF technology is likely reasonable for employing in such on-board vehicle systems as an obesity preventing system to simplify the accurate occupant weighing unit, to improve performance of various safety devices, such as a seat belt and an airbag of a Supplemental Restraint System (SRS system), and other on-board systems that weigh a vehicle occupant.

The following is an example of a possible use of the KEF technology in a SRS system. The author of this application has a SRS system in his car. When he starts the engine of the car, the SRS icon appears on the instrument box display. It seems that SRS tests its parts and weighs the occupant of the vehicle at that time. The weight of the vehicle occupant measured will probably be at least 20%-30% different from the original weight because the feet of the vehicle occupant are on the floor of the vehicle. To make accurate occupant weight measurement at the time of a regular SRS testing, one of the described kemoder approaches of the proposed KEF technology may be used to weigh a driver or passenger in a parked vehicle. By doing this at the time of a regular testing, the SRS system may dramatically advance the accuracy and safety of airbag inflation by different partial speeds of the airbag deploying according to an accurately measured weight of the occupant. The accurate weight of the driver may also be obtained by employing the MEDAL method of the driver weighing when the vehicle is leaving garage, driveway, or parking lot or coasting along.

In another embodiment of the present invention, by employing the accurate and convenient occupant weighing KEF technology, the existing passenger classification system may be improved and a driver classification system may be introduced to avoid possible extra force applied to the occupant's body at the time of collision.

In another embodiment a technology is provided wherein the technology provides a simplified and accurate occupant's weight measurement including weight of the feet by one weighing unit connected to the seat of the vehicle occupant in vehicle safety devices such as seat belt and air bag Supplemental Restraint System (SRS system) to prevent possible extra force applied to the occupant's body in case of collision and to apply to the occupant's body an appropriate force, whose value is calculated according to the accurate measured occupant's weight, by improving the existing Passenger Classification System.

Another exemplary embodiment of the present invention is that it employs a corporate vehicle or bus, limousine, tourist bus, etc. as a part of the obesity preventing system. These vehicles consist of at least one car seat with attached weighing unit. The weighing apparatus employs at least one kemoder according to the convenient elimination of a separate feet weighing KEF technology. There is also a wireless device, such as a smartphone, that is used by one of occupants of these vehicles to take care of the weight measuring procedure. The result of the measurement is wirelessly sent to the Trend Obesity Preventing Service (TOPS) of the obesity preventing system.

FIG. 1 is a block diagram of the on-board vehicle system employing simplified weighing apparatuses for weighing the vehicle occupants. The system includes the following devices: on-board motor vehicle computing and control unit 1, which includes a microcontroller and a smartphone, or may share resources of the on-board computer or any other unit with computing and control resources adequate to the needed resources, a simplified vehicle occupant weighing apparatus 2, which includes a weighing unit 3 connected to the occupant's car seat and weighing moderator (kemoder) 4, communication device 5, in which smartphone is used, a beeper 6 to sound during and at the end of a vehicle occupant weighing, and a heightmeter 8. The microcontroller and smartphone communicate to all devices of the system by use of their memory, routines, and peripheral units. The weighing apparatus 2 may have a direct connection to the communication device 5, in which the smartphone and its downloaded applications are used.

The system starts to work as the vehicle's operator pushes a button of the vehicle keyless remote control outside of the vehicle or after the operator opens the doors of the vehicle. At that moment, the computing and control unit 1 controls the power line and a "zero" calibration of the vehicle occupants' weighing apparatuses.

The vehicle occupant weighing system may work as a stands alone system or as a part of another system that needs to weigh a vehicle occupant, such as a Global Obesity Preventing System (GOPS system) that includes some in-building and on-board vehicle modules or on-board vehicle Supplemental Restraint System (SRS) system. If the described above system, which based on the horwest effect, is a part of a Global Obesity Preventing System (GOPS), it works as a module (HOPS) of the Global Obesity Preventing System (GOP S) system.

When the HOPS collects enough weight measurements of a person that it may calculate in terms of BMI (Body Mass Index) or weight a trend of a person's weight progress, a Weight Trend Analyzer routine 50 (see FIG. 3) downloaded to a computing and control unit is used. When an occupant is a baby or small child, the BMI may be calculated by use of the occupant's height measured by heightmeter 8 secured on the ceiling above the "Child place" car seat to which an appropriate capacity weighing unit is connected. If Weight Trend Analyzer defines that there is an overweight or obesity probability of a person in a short predetermined period of time in the future, the HOPS sends a warning to a person or to a person's primary doctor. The frequency of weight measurements of an occupant depends on his/her age and weight trend rate and is controlled by the operator of the vehicle. Any kind of a wireless communication device 5, which is a smartphone or other device, provides for HOPS ability to send a message that includes the results of the current on-board weight measurements and a warning to a healthcare provider in case of trend to overweight or obesity. When HOPS works as one of modules of GOPS, it sends through the wireless communication device 5 a message that includes the results of the current on-board weight measurements to a Trend Obesity Preventing Service (TOPS) unit 7, which is a part of the GOPS and located outside of the vehicle. Kemoder 4 and beeper 6 are connected to the peripherals of the microcontroller.

Figure 2:
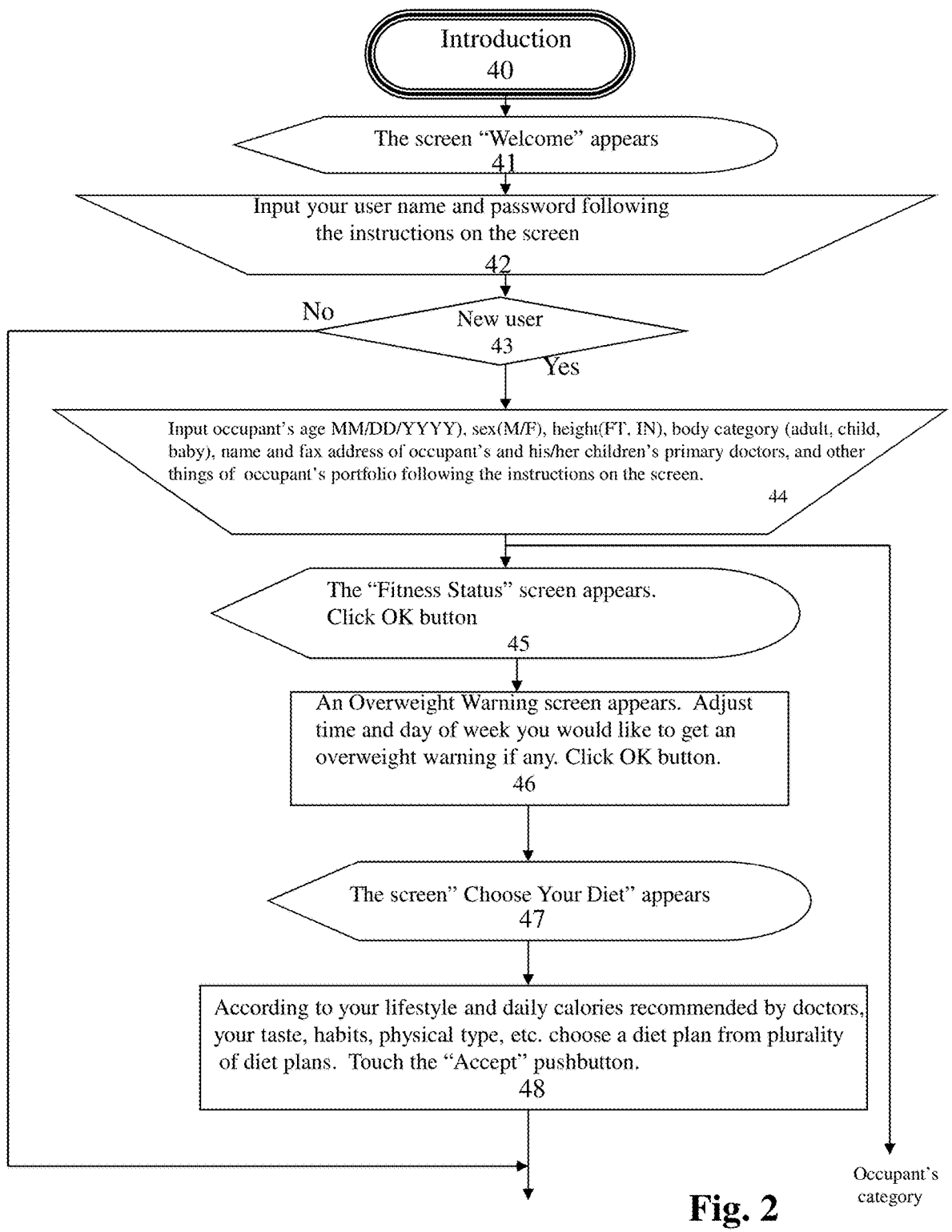
FIG. 2 is a flowchart for the Introduction routine.

FIG. 2 is an Introduction routine algorithm 40. When the system is activated, the screen "Welcome" 41 appears through the Introduction routine. The user is invited to input his/her name and password 42. The system checks the name and password and recognizes if the user is a new user 43. If the user is a new user, the system asks him/her to input 44 name, age, sex, height, names and fax addresses of his/her or his/her children's primary doctor and other things of the portfolio by following the instructions on the screen. After the user has entered the above data, the "Fitness Status" screen appears 45. It shows the weight for the user recommended by the doctors and calories to be consumed per day. The user can use the "Fitness Status" screen to choose the number of pounds to lose daily, and the user will find the number of the calculated days needed to lose extra pounds or the user can choose the number of days he/she wants to lose the extra pounds. In this case, the "Fitness Status" screen will show the calculated pounds to lose daily. An Overweight Warning screen appears 46. A user is invited to enter time and day of week that the user would like to receive an overweight warning, if any. Any outside overweight warning (to user's primary doctor, to his/her child's primary doctor, etc.) may be sent only at user's discretion. The screen "Choose Your Diet" 47 appears. The system suggests 48 to the user to choose a diet plan according to his/her weight, and daily calories recommended by doctors or based upon user's taste, habits, physical type, etc.

Figure 3:
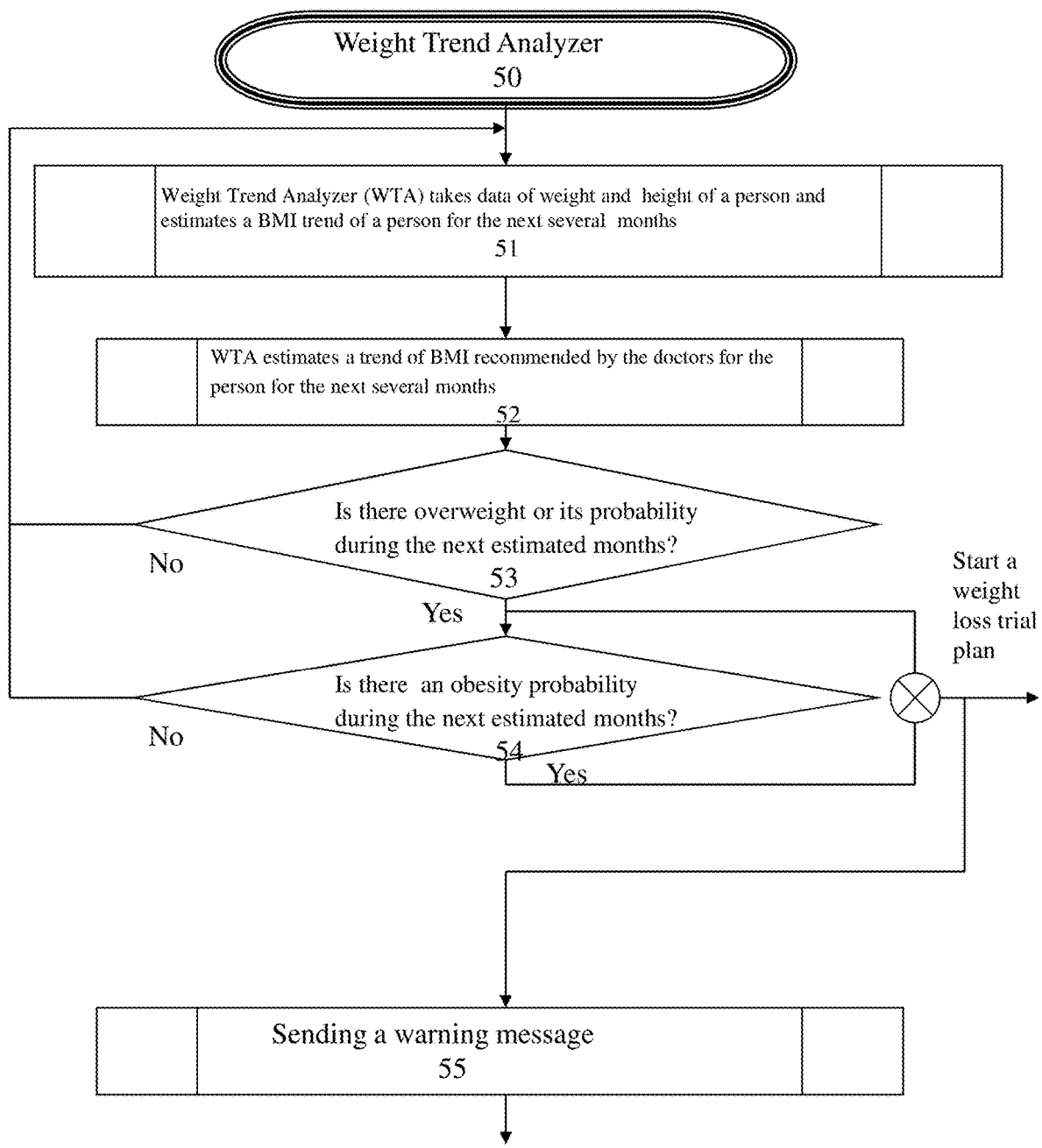
FIG. 3 is a flowchart for the Weight Trend Analyzer routine.

FIG. 3 shows Weight Trend Analyzer routine algorithm 50 that is incorporated into the memory of the computing and control unit 1. When the system collects enough weight measurements of a person that it may calculate a trend of a person's weight progress, Weight Trend Analyzer routine 50 is used. If Weight Trend Analyzer defines that there is an overweight or obesity probability of a person in a short predetermined period of time in the future, the system does not send any warnings to a person or to a person's primary doctor immediately. In contrast, it asks a person to start a weight loss trial plan. If a result of a weight loss plan is negative, the system sends a warning at the person's discretion to the person or/and to a person's primary doctor by use of a communication device 5 (see FIG. 1).

Figure 4:
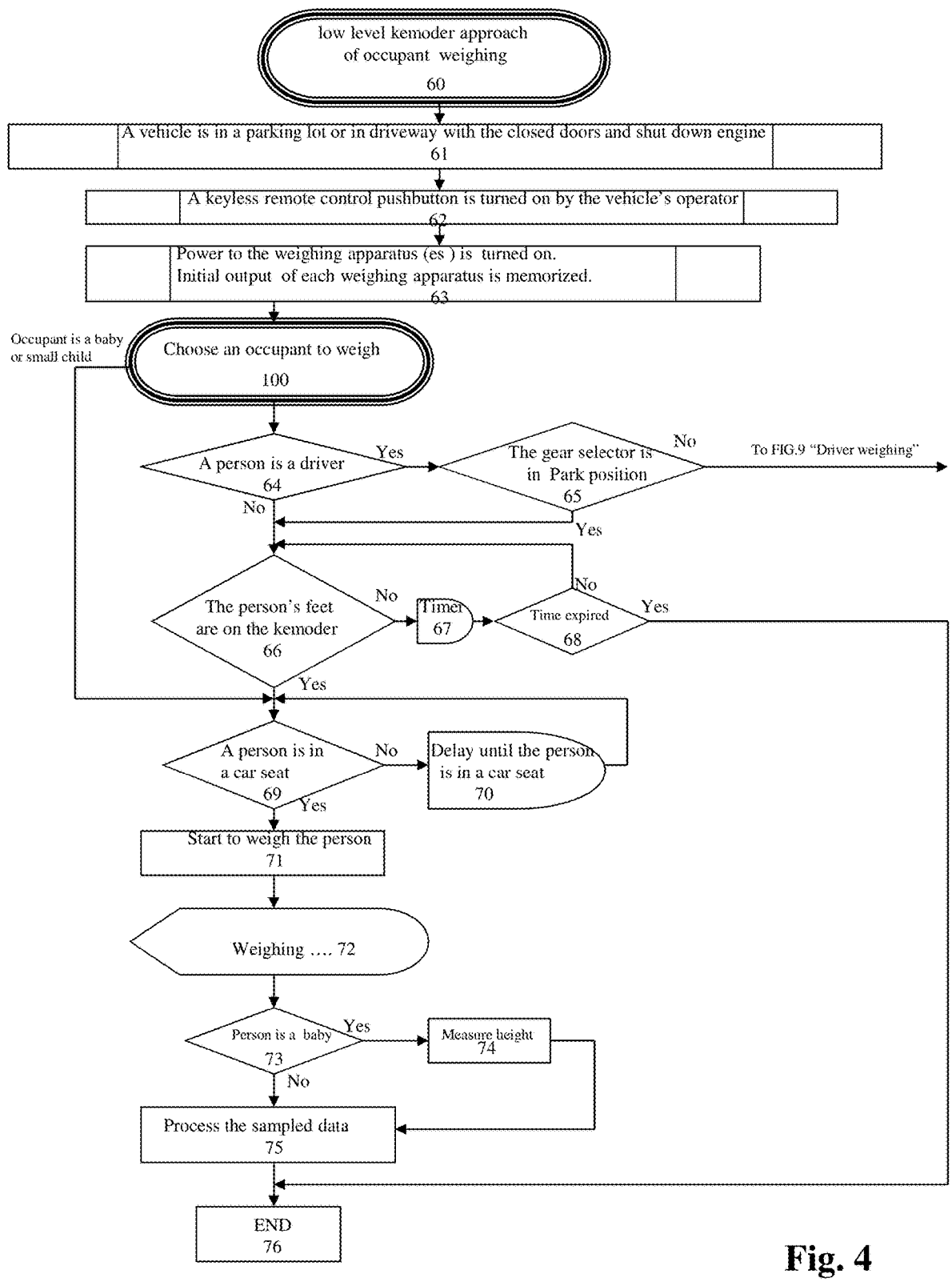
FIG. 4 is a flowchart for the low level kemoder approach of the Vehicle Occupant Weighing routine.

FIG. 4 shows algorithm 60 of a vehicle occupant weighing routine by employing the low level kemoder approach. When the vehicle's operator turns on in 62 a pushbutton of a keyless remote control outside of the vehicle, the power of the weighing apparatus is turned on in 63. Microcontroller or smartphone memorizes the outputs of the weighing units in the occupant's car seats. This data will be used in further processing. After the operator of the vehicle chooses from menu 100 on the screen (see FIG. 5) the car seat and the name of its occupant, who will be weighed, the system checks if a chosen person is a driver or baby or small child. If a person is a baby or small child, the flowchart goes to 69. If this person in 64 is a driver, the position of the gear selector is checked in 65. If a gear selector is not in a Park position, it means that the car is running, and the flowchart leaves routine 60 and goes to FIG. 9 "Driver automatically weighing". If the gear selector of the vehicle is in a Park position in 65, HOPS checks in 66 the existence of the person's feet on a low level kemoder. If the feet are not on kemoder, HOPS waits a predetermined period of time by starting a Timer 67 and checking the time interval in 68. If the time expires, the flowchart leaves routine 60. If the person's feet are on the kemoder, HOPS checks in 69 if a person is in car seat by processing any changes in the data received from the weighing apparatus and continues in 70 to monitor weight of a person until he/she sits down in the car seat. After that, a weighing procedure starts in 71. The collected weight of an occupant in 72 and measured height in 74 (according with a height measurement schedule if a person is a baby or a small child checked in 73) are processed in 75.

Figure 5:
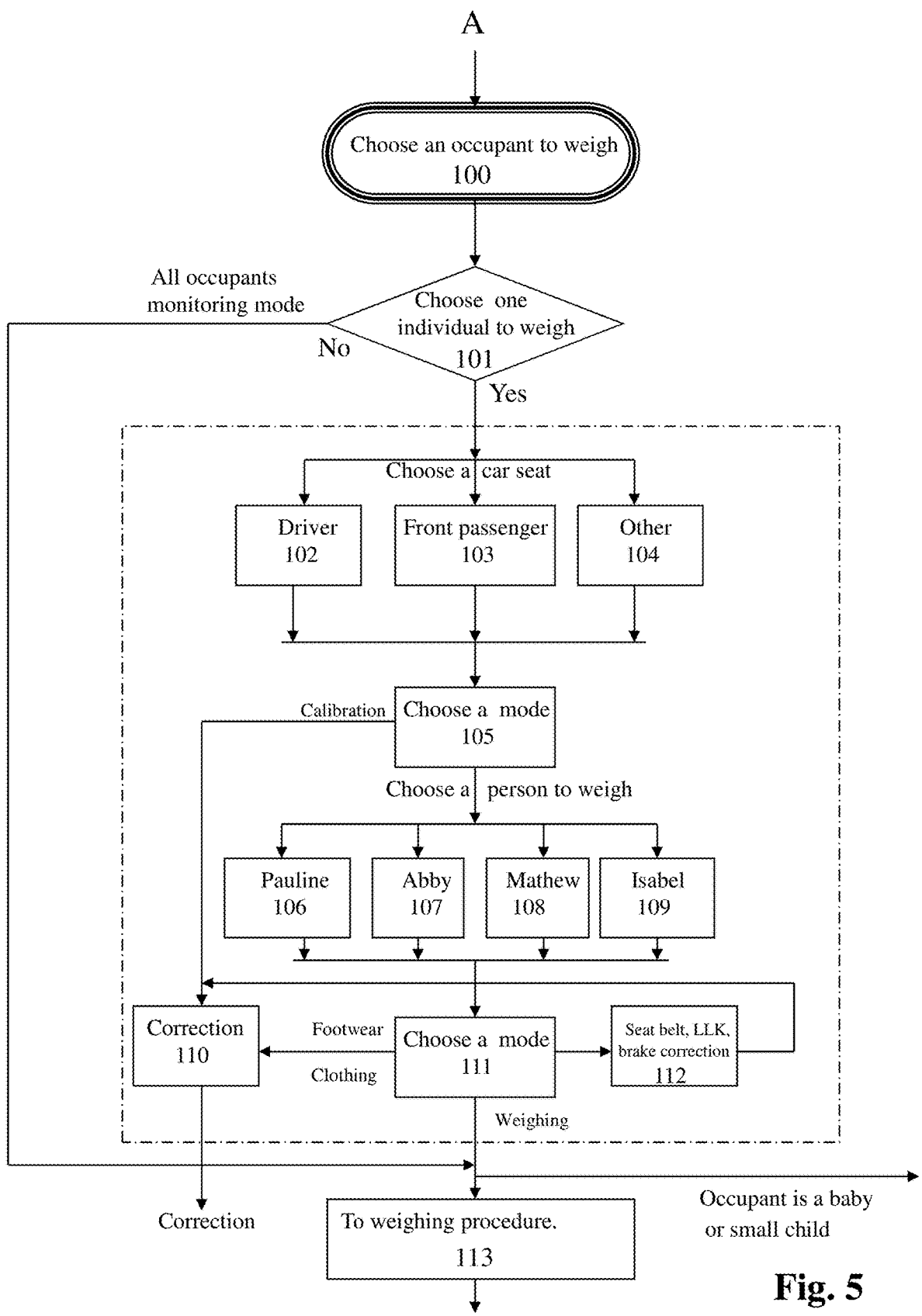
FIG. 5 is a block diagram of a Choose an occupant to weigh algorithm.

FIG. 5 shows a menu on the screen of the "Choose an occupant to weigh" algorithm 100. The operator of the vehicle may choose a car seat with the attached weighing device and may choose a person who will be weighed in this car seat by "Choose an occupant to weigh" screen. For example, in the front passenger car seat, to which a 200 lb capacity weighing apparatus is attached, the operator's 3-year old child may be weighed. Parent has to go through a one-time registration of the child before weighing the child. After registration and the first time weighing, the parent may weigh the child any number of times in any car seat, to which a weighing device is attached by using menu on the "Choose an occupant to weigh" screen 100. The driver of the vehicle in his car seat, to which a weighing apparatus is attached, will be weight by default. The occupant weight samples received during the weighing procedure will be corrected at the time they are processed depending on the statement made by the operator of the vehicle in the steps 105, 111, and 112 of the "Choose an occupant to weigh" screen. There may be several kinds of corrections. A weighing unit in any vehicle seat may be calibrated for more accurate weight measurement at predetermined time by one or more predetermined value weights, whose values are inputted into the computing and control unit by the operator of a vehicle or by a representative of the car service in the calibration mode. Correction for footwear or clothing is made according to the statistics about the weight of the shoes and clothing that depends on occupant's weight, age, and seasonal ambient temperatures, or by measurement of the occupant's footwear or clothing directly in the vehicle. The value of correction of possible small constant errors of weight measurement from the occupant's seat belt (by checking a state of the seat belt switch) and from pushing the low level kemoder (LLK) and from the slight touch of a brake pedal by a driver's right foot may be found and inputted into the computing and control unit once before starting to use the vehicle for each occupant in his/her seat, and this should be repeated in predetermined time. The correction by these values should be made during the regular weight measurements. This routine also sends a signal related to the weight category of the vehicle occupant to the weighing routines.

Figure 6:
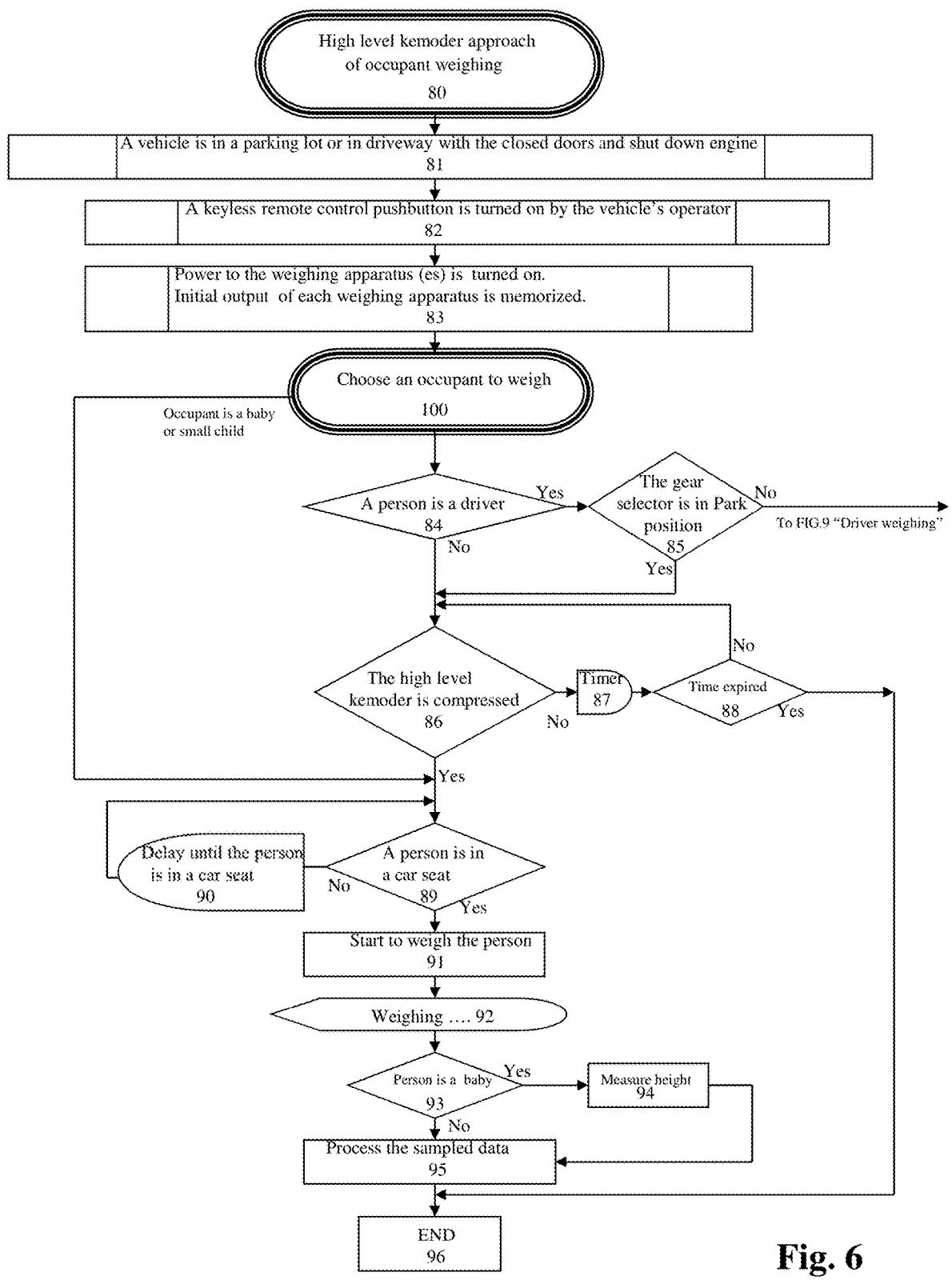
FIG. 6 is a flowchart for the high level kemoder approach of the Vehicle Occupant Weighing routine.

FIG. 6 shows algorithm 80 of a vehicle occupant weighing routine by employing the high level kemoder approach. When the vehicle's operator turns on in 82 a pushbutton of a keyless remote control outside of the vehicle, the power of the weighing apparatus is turned on in 83. Microcontroller or smartphone memorizes the outputs of the weighing units in the occupant's car seats. This data will be used in further processing.

After the operator of the vehicle chooses from menu 100 on the screen (see FIG. 5) the car seat and the name of an occupant, who will be weighed, the system checks if a chosen person is a driver or a baby or small child. If a person a baby or small child, the flowchart goes to 89. If this person in 84 is a driver, the position of the gear selector is checked in 85. If a gear selector is not in a Park position, it means that the car is running, and the flowchart leaves routine 80 and goes to FIG. 8 "Driver automatically weighing". If the gear selector is in a Park position in 85, HOPS checks in 86 the existence of a signal to weigh a person. This signal will appear when the high level kemoder on the steering wheel, dashboard, etc. will be pushed by the occupant, and the occupant will simultaneously lift his/her feet up from the floor. HOPS waits this signal a predetermined period of time by starting a Timer 87 and checking the time interval in 88. If the time expires, the flowchart leaves routine 80. If the high level kemoder is compressed, HOPS checks in 89 if a person is in car seat by processing any changes in the data received from the weighing apparatus. Flowchart waits a predetermined time in 90 until the person will be in the car seat. After that it immediately starts weighing a person if he/she is in a car seat 91. If a person is a baby or small child in 93, his/her height is measured according to the schedule in 94. The collected weight of an occupant in 92 (it will take a couple of seconds) and measured height in 94 (according with a height measurement schedule if a person is a baby or a small child checked in 93) are processed in 95.

Author made a row of experiments related to the horwest effect, KEF technology, hocpoints, kemoders, etc. Besides the simple experiment described on page 6, through which everybody may check how the horwest effect works and how the hocpoints found on the wall and how they work as the simplest high level kemoders, the following several different springs were used for the low level kemoders:

Spring $^{11}/_{16}"\times1^{1}/_{4}"\times0.091"$ (diameter×lengths×thickness of wire) 6 circles (commercially available from HOME DEPOT under item #684838). Spring $^{7}/_{8}"\times4"\times0.08"$ (diameter×lengths×thickness of wire) 6, 9, and 15 circles (commercially available from HOME DEPOT under item #16084).

FIG. 7 shows a table of adults' weight gain from a normal weight status to overweight and to obese weight status depending on a height of a person. The columns in black, copied from a published data, show adults' weight for a normal Body Mass Index status (BMI=22), for an overweight status (BMI=27), and for a not severe obesity status (BMI=32). The column in orange shows the number of extra pounds that an overweight vehicle adult occupant brings in a car relative to the normal weight status, and the pink column shows the number of extra pounds that an obese vehicle occupant brings in a car relative to the normal weight status. It is not hard to calculate how many extra pounds of 60% of American overweight adults "load" every day in cars and how it influences the effectiveness of American cars. The car manufacturers may help prevent this "overload" by very easily checking weight of the occupants in a car and issuing a warning to prevent obesity. In the cars where the weighing devices are installed now (these are the most of American cars), it is necessary just to push a point on a vertical part of the steering wheel or dashboard and simultaneously lift feet very conveniently from the floor for a couple of seconds during the time when the icon of a SRS or another on-board vehicle system that weighs occupants is active on the instrument board. This procedure will cost nothing for the manufacturer and 2-3 seconds for the occupant. These seconds may change the life of a child or adult and improve real effectiveness of American cars. Childhood and teenage years are the most important and the easiest times to do this.

Figure 8:
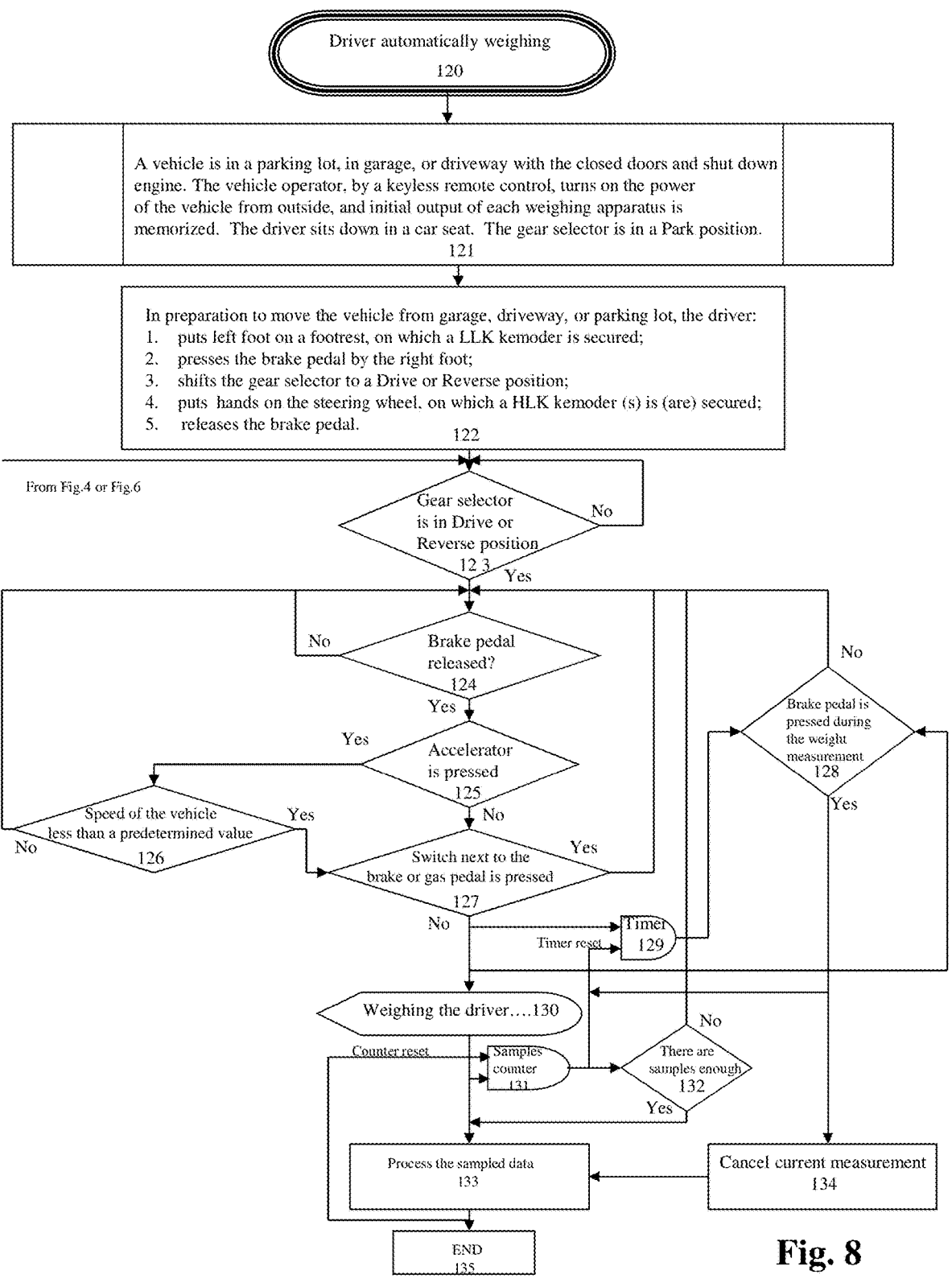
FIG. 8 is a flowchart for the driver automatically weighing in a vehicle leaving the garage, driveway, or parking lot or coasting along.

A driver may be weighed not only in a parked vehicle but in the running vehicle also by employing the MEDAL method of a driver weighing. FIG. 8 shows a flowchart 120 for the driver weighing algorithm in a running vehicle while it is leaving a garage, driveway, or parking lot. This method of driver weighing is safe because the vehicle is running with a small idle speed during the period of time when it is leaving a garage, driveway, or a parking lot, and the MEDAL method is as follows.

When a vehicle is in a garage, driveway, or on a parking lot with the closed doors, the vehicle operator by a keyless remote control turns on the power of the vehicle from outside, and initial output of the weighing apparatus (es) is (are) memorized. The driver sits down in a car seat. The gear selector is in a Park position in 121.

Before driving a vehicle from a garage, driveway, or a parking lot, the driver routinely puts in 122 left foot on the footrest or pedal with a LLK kemoder secured on it, puts right foot on the brake pedal, shifts position of the gear selector from Park to Drive/Reverse (to move the vehicle forward or backward depends on a vehicle position in the garage, driveway, or a parking lot), puts hands on a steering wheel, on which HLK kemoder(s) is (are) secured, and after that said driver slightly releases brake pedal to run the vehicle at the idle speed and, probably, several times in sequence releases and pushes brake pedal until the vehicle leaves the garage, driveway, or parking lot. During this period of time the driver will be weighed by the mentioned above a MEDAL method. The position of a gear selector is checked in 123. If the gear selector is not in Drive or Reverse position, it means that it is still in a Park position. In this case the system waits until the driver shifts gear selector to Drive or Reverse position depending on how the vehicle was parked in the garage, driveway, or parking lot (looking forward or backward). If position of the gear selector is Drive or Reverse it means the vehicle is ready to move, and position of the right foot is checked in 124. If the position of the right foot is still on the brake pedal, the vehicle will not move and future position of the pressed brake is monitored. If driver decided to run the car from the garage, driveway, or parking lot, the brake pedal is released by the right foot of the driver, and the vehicle starts to move at the idle speed from the garage, driveway, or parking lot. When it happens, the right foot of the driver slightly touches the brake pedal or it is in the air. The author measured weight loss in the measured driver's weight, when the right foot of the driver slightly touches the released brake pedal, and on some vehicles it is approximately 1-2 lb. The position of a gas pedal is checked in 125. If the gas pedal is pressed, the speed of the vehicle is checked in 126. If the speed of the vehicle is not greater than a predetermined value, the action goes to 126. In other case it returns to 124. The condition of switches next to the brake and gas pedals is checked in 127. If at least one of them is pressed, the driver will not be weighed because of possible erroneous measurements, and action goes back to 124. If no one of the brake or gas pedal is pressed, the weighing unit connected to the driver's seat starts to measure weight of the driver in 130. Simultaneously, the timer 129 starts to count time interval needed for a weighing unit to complete weighing the driver to get one sample of the weight. If the brake pedal is released and the right foot of the driver slightly touches the brake pedal or it in the air during a time that is longer than time of one weight measurement, the control and computing unit 1 will get one sample of driver's weight in 133, the output number of the samples counter will be increased by one, timer 129 will be reset, and weighing unit will start a next measurement of the driver's weight. Every time the driver releases the brake pedal, the weighing apparatus starts to weigh a driver until the brake pedal will be pressed again. Because the left foot is on a footrest or a pedal, on which is LLK kemoder is secured, and hands of the driver are on the steering wheel, on which HLK kemoders are secured, the weight of the driver according to the horwest effect will not be practically disturbed, and reasonable accurate driver weight measurement will be done.

If during the next weight measurement the brake pedal will be pressed by the right foot of the driver before than the time of one weight measurement elapsed, the control and computing unit 1 removes the current sample of the weight measurement in 128 and 134. If the number of samples is not enough, the weighing procedure will be continued when the brake pedal will be released again and said driver will be weighed several times by on-board simplified apparatus during time intervals when said driver releases the brake pedal (or sequentially releases and pushes the brake pedal several times by right foot) to get the needed number of the samples in 132. The number of collected weight samples will be processed in 135. During processing of collected data the maximum value of the successful measured weight will be employed in the result. The described algorithm of weighing a driver in a running vehicle may work not only during leaving a garage, driveway, or parking lot, but when a vehicle is coasting along on the road too.

In the Table 1 are described recommended, not recommended, and possible ways to weigh an occupant in the parked or running vehicle depending on a category of a vehicle occupant.

TABLE 1

| | Category of a vehicle occupant | | | |
|---|---|---|---|---|
| Position of a vehicle | | A Adults, teens, tall children | B Babies and small children | C Children whose feet don't touch the vehicle floor |
| A parked vehicle | | Driver Recommended | Passenger Recommended | Recommended | Recommended |
| A running vehicle | A vehicle that is leaving a garage, driveway, or parking lot | Recommended | Possible | Not recommended | Possible |
| | A vehicle that is coasting along | Possible | Possible | Not recommended | Possible |

Availability of a weighing device in a vehicle is not only a chance to get weight statistics to predict and prevent overweight and obesity but is a good motivation for the vehicle occupants to check and think about their weight during a trip.

Among several suggested simplified methods of accurately weighing a vehicle occupant the most convenient ones likely are:

For the babies and small children—weighing a passenger in a parked vehicle;

For children, adolescents, and adults—weighing a passenger in a parked or running vehicle;

For a driver—weighing the driver by the MEDAL method in a vehicle leaving a garage, driveway, or parking lot, or in a vehicle that is coasting.

Figure 9:
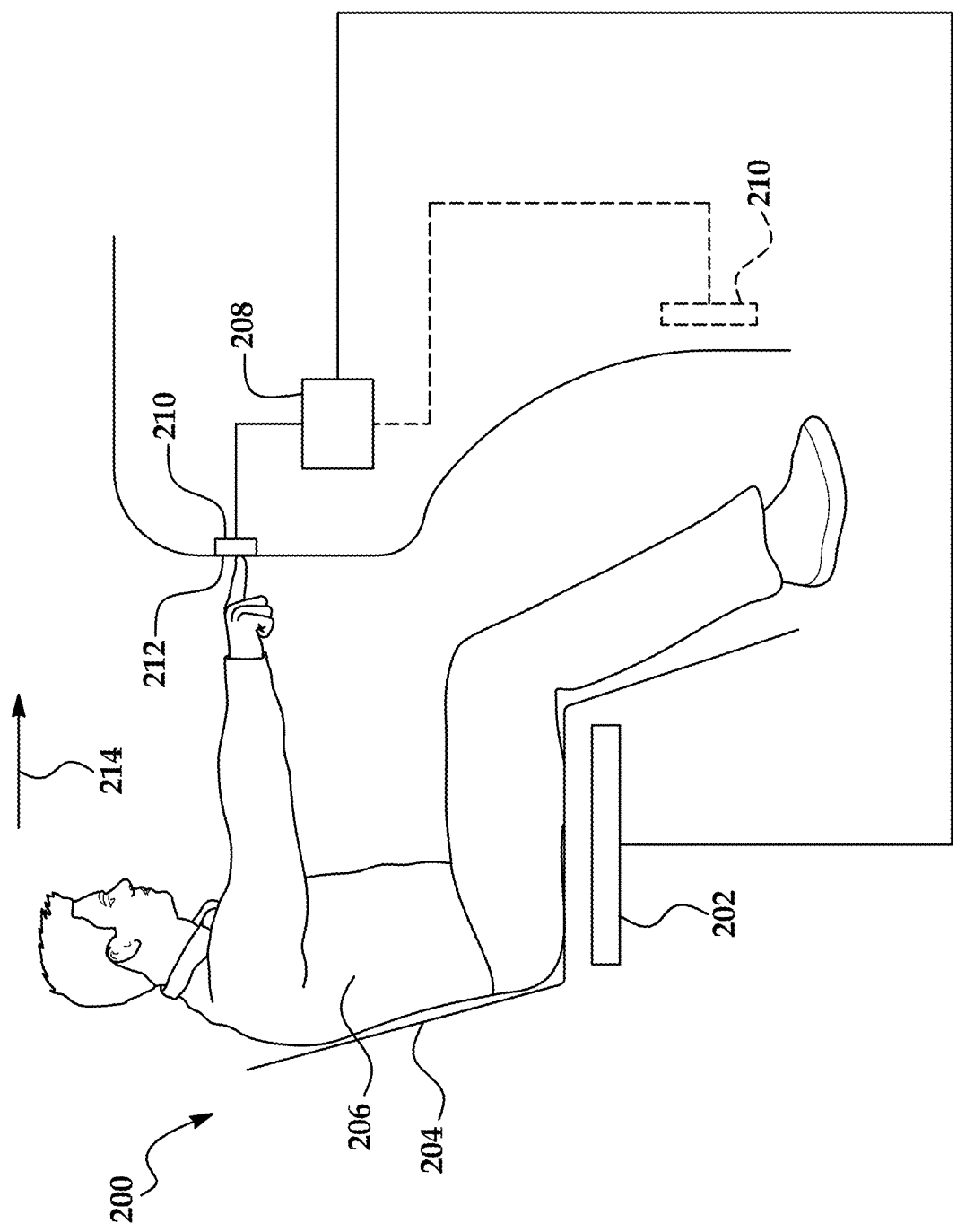
FIG. 9 is a schematic illustration of one non-limiting exemplary embodiment of the present invention.

Referring now to FIG. 9 an on-board occupant weighing system 200 in accordance with one non-limiting exemplary embodiment is illustrated. In one embodiment, the system 200 may be located in a vehicle. The system 200 includes a weighing unit 202 operatively connected to a seat 204 of a vehicle. The weighing unit 202 is configured to provide an output indicative of an occupant's 206 weight when they are seated on the seat 204. The system further may comprise a computing and control unit 208 operatively coupled to the weighing unit 202 and at least one switch 210 operatively coupled to the computing and control unit 208. The switch 210 is behind a vertical surface 212 of the vehicle proximate to the seat 204, wherein the switch 210 is configured to provide an output when a force is applied to the surface 212 of the vehicle proximate to the switch 210 in the horizontal direction of arrow 214, wherein the computing and control 208 unit only processes the output from the weighing unit 202 when the output of the switch 210 is received by the computing and control unit 208.

In an alternative embodiment, the switch 210 may be located proximate to an occupant's feet so the force in the direction of arrow 214 can be applied by their feet, alternatively the switch 210 may be located proximate to the occupant's hand and the force is applied by their hand in the direction of arrow 214. Still further and in yet another embodiment, there may be two switches one proximate to the feet and one proximate to the hands and the force in the direction of arrow 214 may be applied in by either the hand(s) or the feet or foot or both the hand(s) and the feet or foot.

It being understood that computing and control unit 208 includes a microprocessor, microcontroller or other equivalent processing device capable of executing commands of computer readable data or program for executing a control algorithm that controls the operation of the system 200 in order to perform the prescribed functions and desired processing, as well as the computations therefore (e.g., the execution of fourier analysis algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the described features.

What is claimed is:

1. A method of weighing a person sitting in a seat of a vehicle, comprising:
    applying a force in a first horizontal direction of a predetermined value with respect to a substantially vertical surface of an object that is a predetermined distance away from a weighing unit operatively coupled to the seat of the vehicle, wherein application of the force in the horizontal direction does not change a weight measurement of the person recorded by the weighing unit when the person is applying the force in the horizontal direction to the vertical surface;
    compressing in a second horizontal frontal direction at least one of a plurality of switches, located above a waist of the person and located on a substantially vertical part of the vehicle; and
    lifting feet of the person above a floor of the vehicle during weight measurement of the person; and
    signaling a result of the weight measurement to an on-board computing and control unit of the vehicle when the feet of the person are above the floor of the vehicle and one of the plurality of switches is compressed.

2. A method of weighing a person as in claim 1, wherein the vehicle is a school bus and the person is a student on the school bus, the method comprising the steps of:
    receiving personal information of the student by an on-board computing and control unit or a smartphone of a driver of the school bus or a health care person in the school bus that stores the personal information of the student;
    choosing by the on-board computing and control unit or smartphone a location of a bus seat or scale to weigh student in the school bus;
    measuring a weight of the student with the scale that is located on a floor of the school bus or by a weighing unit connected to the bus seat of the student in the school bus;
    eliminating the need to separately weigh the student's feet, while weighing the student by compressing in horizontal direction a switch of a weighing moderator located on a substantially vertical surface in front of student's hands;
    simultaneously lifting the student's feet above the floor of the school bus during a weight measurement of the student;
    measuring a height of the student by a heightmeter located on a ceiling of the school bus;
    receiving the student's weight and height with the on-board computing and control unit or the smartphone;
    processing a collected weight of the student by the on-board computing and control unit or smartphone while receiving the signals from the switch of the weighing moderator;
    sending the result of the weight and height measurements of the student to the school obesity preventing system by the smartphone;
    determining the probability of an overweight or obesity condition in a predetermined time of the student by a weight trend analyzer executed by the smartphone or the on-board computing and control unit;
    upon forecasting the overweight or obesity condition of the student, sending a warning about the overweight or obesity condition of the student to one of: the student's parent, a school nurse, and the student's primary health care provider; and
    erasing previous weight measurements of another student of the school bus from the driver's smartphone.

3. A method of weighing a person as in claim 1, wherein the vehicle is one of a corporate vehicle, a corporate bus, a limousine, and a tourist bus comprising the steps of:
    logging in by a registered occupant of the vehicle into an on-board vehicle overweight and obesity preventing system by the registered occupant's smartphone;
    receiving the registered occupant's personal information by the on-board vehicle overweight and obesity preventing system, wherein the registered occupant's smartphone stores the registered occupant's personal information;
    measuring a weight of the registered occupant's by the weighing unit;
    receiving the registered occupant's weight with the smartphone;
    processing collected weight of the registered occupant by the smartphone while receiving a signal from the plurality of switches;
    showing a graph of weight or BMI trend of the registered occupant on a screen of the smartphone of the registered occupant;
    sending a result of the weight measurement of the registered occupant to a company obesity preventing system by the smartphone;
    determining the probability of an overweight or obesity in a predetermined short period of time of the registered occupant by a weight trend analyzer executed by the smartphone;
    upon forecasting an overweight or obesity condition of the registered occupant, sending a warning about the overweight or obesity condition to the registered occupant on the screen of the registered occupant's smartphone and to the registered occupant's primary doctor at the registered occupant's discretion wirelessly by the register occupant's smartphone.

4. A method of operating an on-board vehicle overweight and obesity preventing system as in claim 1, wherein the person is a baby or small child, the method comprising the steps of:
   receiving the baby's or the small child's personal information, wherein an on-board computing and control unit shares the baby's or the small child's personal information with a smartphone;
   choosing from a menu a name of the baby or the small child and a position or number of a car seat to which a weighing unit is connected and in which the baby or the small child will be weighed and above which a heightmeter is secured on a ceiling the vehicle;
   measuring a height of the baby or the small child with the heightmeter;
   measuring a weight of the baby or the small child with the weighing unit;
   receiving the baby's or the small child's weight with the on-board computing and control unit and the smartphone;
   calculating the baby's or the small child's weight, height, and BMI with the on-board computing and control unit and the smartphone;
   sending the results of the weight and height measurements of the baby or the small child to an obesity preventing system where the baby or the small child is registered;
   determining a probability of an overweight or an obesity condition in a predetermined period of time of the baby or the small child by the obesity preventing system;
   upon forecasting an overweight or an obesity condition of the baby or the small child by the obesity preventing system, sending a warning about the overweight or the obesity condition to a parent of the baby or the small child locally or to the baby's or small child's primary doctor by a wireless communication device or a smartphone.

5. A method of weighing a person as in claim 1, comprising:
   monitoring a state of the vehicle when it has not moved from a garage, a driveway, or a parking lot by:
   confirming with a signal from a gear selector of the vehicle that the vehicle is in a park position;
   confirming that the person is in the seat by a signal from the weighing unit attached to the seat,
   confirming that a foot of the person is on the substantially vertical surface by a signal from a switch of the weighing unit;
   confirming that another foot of the person is on a brake pedal by a signal from the brake pedal;
   confirming that the gear selector has been changed from park to a drive/reverse position;
   storing the person's weight measurements to a computing and control unit from an output of the weighing unit connected to the seat while signals from the gas pedal and the brake pedal indicate that the foot and the another foot are no longer on the gas pedal and the brake pedals;
   processing the weight measurements of the person by the computing and control unit or the smartphone;
   showing a graph of weight or BMI trend of person on a screen of the on-board computing and control unit or the smartphone;
   determining a probability of an overweight condition or an obesity condition in a predetermined of time of the person by a weight trend analyzer, wherein the determining step is executed by the on-board computing and control unit or the smartphone;
   upon forecasting the overweight or the obesity condition, sending a warning to the person and the person's primary doctor by a wireless communication device.

* * * * *